(12) United States Patent
Kim et al.

(10) Patent No.: US 7,279,568 B2
(45) Date of Patent: Oct. 9, 2007

(54) HIGHLY EFFICIENT EUKARYOTIC EXPRESSION VECTOR COMPRISING AN EXOGENOUS TRANSCRIPTION REGULATORY ELEMENT

(75) Inventors: Sunyoung Kim, Seoul (KR); Seung-Shin Yu, Seoul (KR)

(73) Assignee: ViroMed Limited (KR)

( * ) Notice: Subject to any disclaimer, the term of this patent is extended or adjusted under 35 U.S.C. 154(b) by 623 days.

(21) Appl. No.: 10/431,121

(22) Filed: May 6, 2003

(65) Prior Publication Data

US 2003/0229046 A1     Dec. 11, 2003

(51) Int. Cl.
    C07H 21/04     (2006.01)
(52) U.S. Cl. .................. 536/24.1; 435/69.1; 435/69.7; 435/252.3; 435/320.1; 435/325
(58) Field of Classification Search ............... 536/24.1; 435/320.1
    See application file for complete search history.

(56) References Cited

U.S. PATENT DOCUMENTS 5,830,879 A * 11/1998 Isner ........................... 514/44

FOREIGN PATENT DOCUMENTS

| EP | 0 255 320 | 7/1987 |
|---|---|---|
| WO | WO 89/01036 | 2/1989 |
| WO | WO 00/40737 A1 | 7/2000 |

OTHER PUBLICATIONS

Dong Wan Kim, et al., "An efficient expression vector for stable expression in human live "r Gene134 (1993), 307-308.
N. Wakabayashi-Ito, et al., "Characterization of the Regulatory Elements in the Promoter of the Human Elongation Factor 1-a Gene", The Journal of Biological Chemistry, vol. 269, No. 47, Issue of Nov. 25, pp. 29831-29837, (1994).
J. Byun, et al., "Analysis of the relative level of gene expression from different retroviral vectors used for gene therapy", Gene Therapy (1996) 3, 780-788.
S. Takeshita, et al., "A Single Intraarterial Bolus of Vascular Endothelial Growth Factor Augments Revascularization in a Rabbit Ischemic Hind Limb Model", Therapeutic Anglogenesis, vol. 93, Feb. 1994, 662-670 (1994).
Dong Wan Kim, et al., "Use of the human elongation factor 1a promoter as a versatile and efficient expression system", Gene 91 (1990) 217-223.
BS Chapman, et al., "Effect of intron A from human cytomegalovirus (Towne) immediate-early gene on heterologous expression in mammalian cells", Nucleic Acids Research, vol. 19, No. 14, 3979-3986, (1991).
Wirth Manfred, et al., "Construction of new expression vectors for mammalian cells using the immediate early enhancer of the human cytomegalovirus to increase expression from heterologous enhancer/promoters", GBF Monographs, vol. 15, 1991, pp. 49-52, XP-001119558, Intl. workshop on Protein Glycosylation, Braunschweig, Germany, Jun. 28-30, 1990.
A. Akrigg, et al., "The structure of the major immediate early gene of human cytomegalovirus strain AD169", Virus Research, 2 (1985) 107-121.
Addison et al., 1987, "Comparison of the human versus murine cytomegalovirus immediate early game promoters for transgene expression by adenoviral vectors", Journal of General Virology 78:1853-1861.
Blegalke & Gaballe, 1991, "Sequence Requirements for Activation of the HIV-1 LTR by Human Cytomegalovirus", Virology 183:381-385.
Cannon et al., 1996, "Murine Leukemia Virus-Based Tal-Inducible Long Terminal Repeat Replacement Vectors: a New System for Anti-Human Immunodeficiency Virus Gene Therapy", Journal of Virology 70(11):8234-8240.
Damanla et al., 1998, "Simian Virus 40 Large T Antigen Stabilizes the TATA-Binding Protein-TFIIA Complex on the TATA Element", Molecular and Cellular Biology 18(7):3926-3935.
DuBridge et al., 1987, "Analysis of Mutation in Human Cells by Using an Epstein-Barr Virus Shuttle System", Molecular and Cellular Biology 7(1):379-387.
Gillinger & Alwine, 1993, "Transcriptional Activation by Simian Virus 40 Large T Antigen: Requirements for Simple Promoter Structures Containing either TATA or Initiator Elements with Variable Upstream Factor Binding Sites", Journal of Virology 67(11):6882-6888.
Gruda et al., 1993, "Transcriptional Activation by Simian Virus 40 Large T Antigen: Interactions with Multiple Component of the Transcription Complex", Molecular and Cellular Biology 13(2):981-989.
Kim et al., 1998, "Construction of Retroviral Vectors with Improved Safety, Gene Expression, and Versatility", Journal of Virology 72(2):984-1004.
Kozak, 1991, "Structural Features In Eukaryatic mRNAs that Modulate the Initiation of Translation", Journal of Biological Chemistry 256(30):19867-19870.
Takekoshi et al., 1998, "Use of a Glycoprotein gB Promoter for Expression of Genes Inserted into the Human Cytomegalovirus Genoma", Total J. Exp. Clin. Med., 23(1):37-42.
Uetsuki et al, 1989, "Isolation and Characterization of the Human Chromosomal Gene for Polypeptide Chain Elongation Factor-1α", Journal of Biological Chemistry 264(10):5791-5798.

* cited by examiner

*Primary Examiner*—J. E. Angell
(74) *Attorney, Agent, or Firm*—Anderson Kill & Olick, PC

(57) ABSTRACT

The present invention relates to a highly efficient eukaryotic expression vector containing an exogenous transcription regulatory element which comprises a promoter/enhancer and the nucleotide sequence upstream of the translation initiation codon derived from human cytomegalovirus (HCMV) immediately early (IE) gene or human elongation factor 1α (EF1α) gene.

Figure 1:
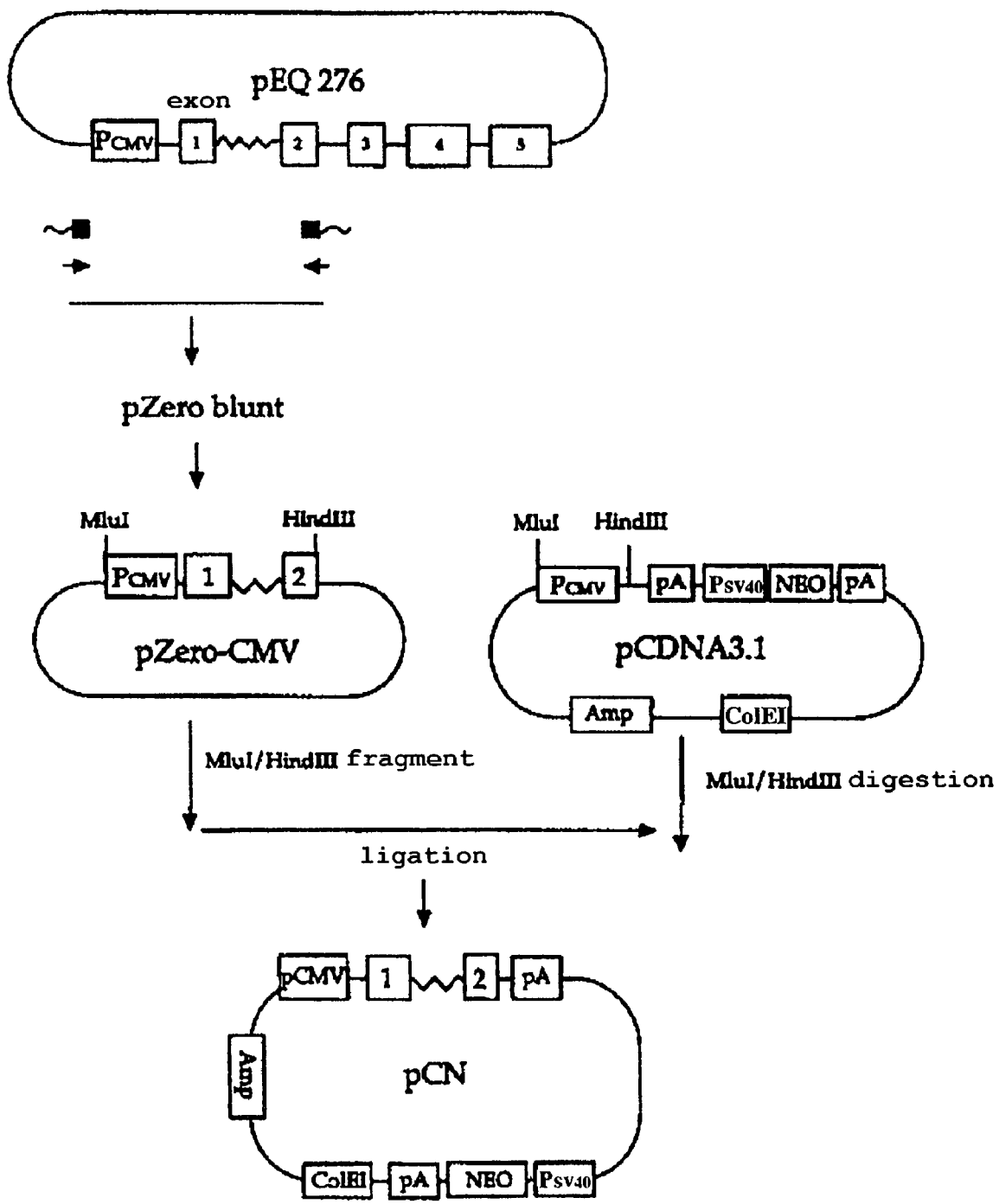

30 Claims, 30 Drawing Sheets

SEQUENCE LISTING

```
<160> NUMBER OF SEQ ID NOS: 19
<210> SEQ ID NO 1
<211> LENGTH: 21
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (1)..(6)
<223> OTHER INFORMATION: MluI restriction enzyme site

<400> SEQUENCE: 1
acgcgttgac attgattatt g                                        21

<210> SEQ ID NO 2
<211> LENGTH: 21
<212> TYPE: DNA
<213> ORGANISM: Artificial Sequence
<220> FEATURE:
<223> OTHER INFORMATION: reverse primer
<220> FEATURE:
```

<221> NAME/KEY: misc_feature
<222> LOCATION: (1)..(6)
<223> OTHER INFORMATION: HindIII restriction enzyme site

<400> SEQUENCE: 2
aagcttcgtg tcaaggacgg t                                           21

<210> SEQ ID NO 3
<211> LENGTH: 1567
<212> TYPE: DNA
<213> ORGANISM: Human cytomegalovirus (HCMV) immediate early (IE) gene
<220> FEATURE:
<221> NAME/KEY: promoter
<222> LOCATION: (1)..(599)
<223> OTHER INFORMATION: HCMV promoter
<220> FEATURE:
<221> NAME/KEY: exon
<222> LOCATION: (600)..(720)
<223> OTHER INFORMATION: exon 1
<220> FEATURE:
<221> NAME/KEY: intron
<222> LOCATION: (721)..(1547)
<223> OTHER INFORMATION: intron A
<220> FEATURE:
<221> NAME/KEY: exon
<222> LOCATION: (1548)..(1564)
<223> OTHER INFORMATION: 5'-UTR of exon 2

<400> SEQUENCE: 3
tgacattgat tattgactag ttattaatag taatcaatta cggggtcatt agttcatagc    60
ccatatatgg agttccgcgt tacataactt acggtaaatg gcccgcctgg ctgaccgccc   120
aacgaccccc gcccattgac gtcaataatg acgtatgttc ccatagtaac gccaataggg   180
actttccatt gacgtcaatg ggtggagtat ttacggtaaa ctgcccactt ggcagtacat   240
caagtgtatc atatgccaag tacgccccct attgacgtca atgacggtaa atggcccgcc   300
tggcattatg cccagtacat gaccttatgg gactttccta cttggcagta catctacgta   360
ttagtcatcg ctattaccat ggtgatgcgg ttttggcagt acatcaatgg gcgtggatag   420
cggtttgact cacggggatt tccaagtctc cacccattg acgtcaatgg gagtttgttt    480
tggcaccaaa atcaacggga ctttccaaaa tgtcgtaaca actccgcccc attgacgcaa   540
atgggcggta ggcgtgtacg gtgggaggtc tatataagca gagctcgttt agtgaaccgt   600
cagatcgcct ggagacgcca tccacgctgt tttgacctcc atagaagaca ccgggaccga   660
tccagcctcc gcggccggga acggtgcatt ggaacgcgga ttccccgtgc caagagtgac   720
gtaagtaccg cctatagagt ctataggccc acccccttgg cttcttatgc atgctatact   780
gtttttggct tggggtctat acaccccgc ttcctcatgt tataggtgat ggtatagctt    840
agcctatagg tgtgggttat tgaccattat tgaccactcc cctattggtg acgatacttt   900
ccattactaa tccataacat ggctctttgc cacaactctc tttattggct atatgccaat   960
acactgtcct tcagagactg acacggactc tgtatttta caggatgggg tctcatttat   1020
tatttacaaa ttcacatata caacaccacc gtccccagtg cccgcagttt ttattaaaca   1080
taacgtggga tctccacgcg aatctcgggt acgtgttccg gacatgggct cttctccggt   1140
agcggcggag cttctacatc cgagccctgc tccatgcct ccagcgactc atggtcgctc    1200
ggcagctcct tgctcctaac agtggaggcc agacttaggc acagcacgat gcccaccacc   1260
accagtgtgc cgcacaaggc cgtggcggta gggtatgtgt ctgaaaatga gctcggggag   1320
cgggcttgca ccgctgacgc atttggaaga cttaaggcag cggcagaaga agatgcaggc   1380
agctgagttg ttgtgttctg ataagagtca gaggtaactc ccgttgcggt gctgttaacg   1440

```
gtggagggca gtgtagtctg agcagtactc gttgctgccg cgcgcgccac cagacataat    1500
agctgacaga ctaacagact gttcctttcc atgggtcttt tctgcagtca ccgtccttga    1560
cacgatg                                                              1567
```

```
<210> SEQ ID NO 4
<211> LENGTH: 36
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (1)..(6)
<223> OTHER INFORMATION: MluI restriction enzyme site

<400> SEQUENCE: 4
acgcgtggca attgaaccgg tgcctagaga aggtgg                              36

<210> SEQ ID NO 5
<211> LENGTH: 36
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (1)..(6)
<223> OTHER INFORMATION: NheI restriction enzyme site

<400> SEQUENCE: 5
gctagctttg gcttttaggg gtagttttca cgacac                              36

<210> SEQ ID NO 6
<211> LENGTH: 1139
<212> TYPE: DNA
<213> ORGANISM: Human EF1-alpha gene
<220> FEATURE:
<221> NAME/KEY: promoter
<222> LOCATION: (1)..(137)
<223> OTHER INFORMATION: human EF1-alpha promoter
<220> FEATURE:
<221> NAME/KEY: exon
<222> LOCATION: (138)..(158)
<223> OTHER INFORMATION: exon 1
<220> FEATURE:
<221> NAME/KEY: intron
<222> LOCATION: (159)..(1104)
<223> OTHER INFORMATION: intron A
<220> FEATURE:
<221> NAME/KEY: exon
<222> LOCATION: (1105)..(1136)
<223> OTHER INFORMATION: 5'-UTR of exon 2

<400> SEQUENCE: 6
ggcaattgaa ccggtgccta gagaaggtgg cgcggggtaa actgggaaag tgatgtcgtg     60
tactggctcc gcctttttcc cgagggtggg ggagaaccgt atataagtgc agtagtcgcc    120
gtgaacgttc tttttcgcaa cgggtttgcc gccagaacac aggtaagtgc cgtgtgtggt    180
tcccgcgggc ctggcctctt tacgggttat ggcccttgcg tgccttgaat tacttccacg    240
cccctggctg cagtacgtga ttcttgatcc cgagcttcgg gttggaagtg ggtgggagag    300
ttcgaggcct tgcgcttaag gagccccttc gcctcgtgct tgagttgagg cctggcctgg    360
gcgctggggc cgccgcgtgc gaatctggtg gcaccttcgc gcctgtctcg ctgctttcga    420
taagtctcta gccatttaaa attttgatg acctgctgcg acgctttttt tctggcaaga    480
```

```
tagtcttgta aatgcgggcc aagatctgca cactggtatt tcggtttttg gggccgcggg      540
cggcgacggg gcccgtgcgt cccagcgcac atgttcggcg aggcggggcc tgcgagcgcg      600
gccaccgaga tcggacgggg ggtagtctca agctggccgg cctgctctgg tgcctggcct      660
cgcgccgccg tgtatcgccc cgccctgggc ggcaaggctg gcccggtcgg caccagttgc      720
gtgagcggaa agatggccgc ttcccggccc tgctgcaggg agctcaaaat ggaggacgcg      780
gcgctcggga gagcgggcgg gtgagtcacc cacacaaagg aaaagggcct ttccgtcctc      840
agccgtcgct tcatgtgact ccacggagta ccgggcgccg tccaggcacc tcgattagtt      900
ctcgagcttt tggagtacgt cgtctttagg ttggggggag gggttttatg cgatggagtt      960
tccccacact gagtgggtgg agactgaagt taggccagct tggcacttga tgtaattctc     1020
cttggaattt gcccttttg agtttggatc ttggttcatt ctcaagcctc agacagtggt     1080
tcaaagtttt tttcttccat ttcaggtgtc gtgaaaacta cccctaaaag ccaaaaatg     1139

<210> SEQ ID NO 7
<211> LENGTH: 27
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (1)..(5)
<223> OTHER INFORMATION: BglII restriction enzyme site

<400> SEQUENCE: 7
agatctacgc gttgacattg attattg                                           27

<210> SEQ ID NO 8
<211> LENGTH: 25
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (1)..(6)
<223> OTHER INFORMATION: HpaI restriction enzyme site

<400> SEQUENCE: 8
gttaactcta taggcggtac ttacg                                             25

<210> SEQ ID NO 9
<211> LENGTH: 18
<212> TYPE: DNA
<213> ORGANISM: Artificial Sequence
<220> FEATURE:
<223> OTHER INFORMATION: forward primer

<400> SEQUENCE: 9
atgaactttc tgctgtct                                                     18

<210> SEQ ID NO 10
<211> LENGTH: 24
<212> TYPE: DNA
<213> ORGANISM: Artificial Sequence
<220> FEATURE:
<223> OTHER INFORMATION: reverse primer

<400> SEQUENCE: 10
tcacctcggc ttgtcacatt tttc                                              24
```

```
<210> SEQ ID NO 11
<211> LENGTH: 21
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (1)..(6)
<223> OTHER INFORMATION: MluI restriction enzyme site

<400> SEQUENCE: 11
acgcgttgac attgattatt g                                              21

<210> SEQ ID NO 12
<211> LENGTH: 30
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (1)..(6)
<223> OTHER INFORMATION: SalI restriction enzyme site

<400> SEQUENCE: 12
gtcgactccc cagcatgcct gctattgtct                  30

<210> SEQ ID NO 13
<211> LENGTH: 24
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (1)..(6)
<223> OTHER INFORMATION: HindIII restriction enzyme site

<400> SEQUENCE: 13
aagcttatga actttctgct gtct                        24

<210> SEQ ID NO 14
<211> LENGTH: 30
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (1)..(6)
<223> OTHER INFORMATION: XbaI restriction enzyme site

<400> SEQUENCE: 14
tctagatcac cgcctcggct tgtcacatca                  30

<210> SEQ ID NO 15
<211> LENGTH: 24
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (1)..(6)
<223> OTHER INFORMATION: HindIII restriction enzyme site

<400> SEQUENCE: 15
aagcttgacg gtgactgcag aaaa                        24
```

```
<210> SEQ ID NO 16
<211> LENGTH: 24
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (1)..(6)
<223> OTHER INFORMATION: NheI restriction enzyme site

<400> SEQUENCE: 16
gctagcgcaa ccctgggaga cgtc                              24

<210> SEQ ID NO 17
<211> LENGTH: 26
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (1)..(8)
<223> OTHER INFORMATION: NotI restriction enzyme site

<400> SEQUENCE: 17
gcggccgcac tgaccctct gagcat                             26

<210> SEQ ID NO 18
<211> LENGTH: 24
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (1)..(6)
<223> OTHER INFORMATION: NheI restriction enzyme site

<400> SEQUENCE: 18
gctagcgcca ccatggcgcg ttca                              24

<210> SEQ ID NO 19
<211> LENGTH: 26
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (1)..(8)
<223> OTHER INFORMATION: NotI restriction enzyme site

<400> SEQUENCE: 19
gcggccgcga tatctcatgg ctcgta                            26
```

HIGHLY EFFICIENT EUKARYOTIC EXPRESSION VECTOR COMPRISING AN EXOGENOUS TRANSCRIPTION REGULATORY ELEMENT

FIELD OF THE INVENTION

The present invention relates to a highly efficient eukaryotic expression vector containing an exogenous transcription regulatory element which comprises a promoter/enhancer and the nucleotide sequence upstream of the translation initiation codon derived from human cytomegalovirus (HCMV) immediately early (IE) gene or human elongation factor 1α (EF1α) gene.

BACKGROUND OF THE INVENTION

Gene Therapy is an innovative form of medicine. Among several gene delivery vectors currently used in gene therapy trials, naked DNA alone or in combination with others such as liposome, electroporation, or gene gun is employed in almost 25% of approved clinical protocols. Naked DNA, when used alone, is probably the safest and the most convenient form of gene delivery vector. However, its approach has been limited because of its low level of gene expression.

In addition, one of major limiting factors for its large scale clinical application is the low expression level of a therapeutic protein at a given amount of DNA injected to a target site. In previous gene therapy trials, 4 mg of DNA in total was applied to a patient, 2 mg each with an interval of 4 weeks. This is a relatively large amount of DNA and as such, it may contribute to high production costs. The best way of making naked DNA gene therapy affordable is to use an expression system that not only drive the highest possible level of therapeutic protein and but also yield the highest possible copy number in *E. coli*.

The present inventors have therefore endeavored to meet the above need, and developed a highly efficient eukaryotic expression vector containing an exogenous transcription regulatory element which comprises a promoter/enhancer and the nucleotide sequence upstream of the translation initiation codon derived from HCMV IE gene or human EF1α gene.

SUMMARY OF THE INVENTION

Accordingly, an object of the present invention is to provide a highly efficient eukaryotic expression vector for gene therapy which comprises a transcription regulatory element for effectuating gene expression both in in vivo and in vitro expression systems.

In accordance with one aspect of the present invention, there is provided a eukaryotic expression vector containing a multi-cloning site, a poly A signal, a selectable marker gene, a ColE1 origin of replication and a transcription regulatory element comprised of a promoter/enhancer and the nucleotide sequence upstream of the translation initiation codon derived from the HCMV IE gene or the human EF1α gene.

In accordance with another aspect of the present invention, there are provided cells transformed with said eukaryotic expression vector.

In accordance with still another aspect of the present invention, there is provided a composition for gene therapy comprising said eukaryotic expression vector introduced with a therapeutic gene as an effective ingredient.

BRIEF DESCRIPTIONS OF THE INVENTION

Figure 2:
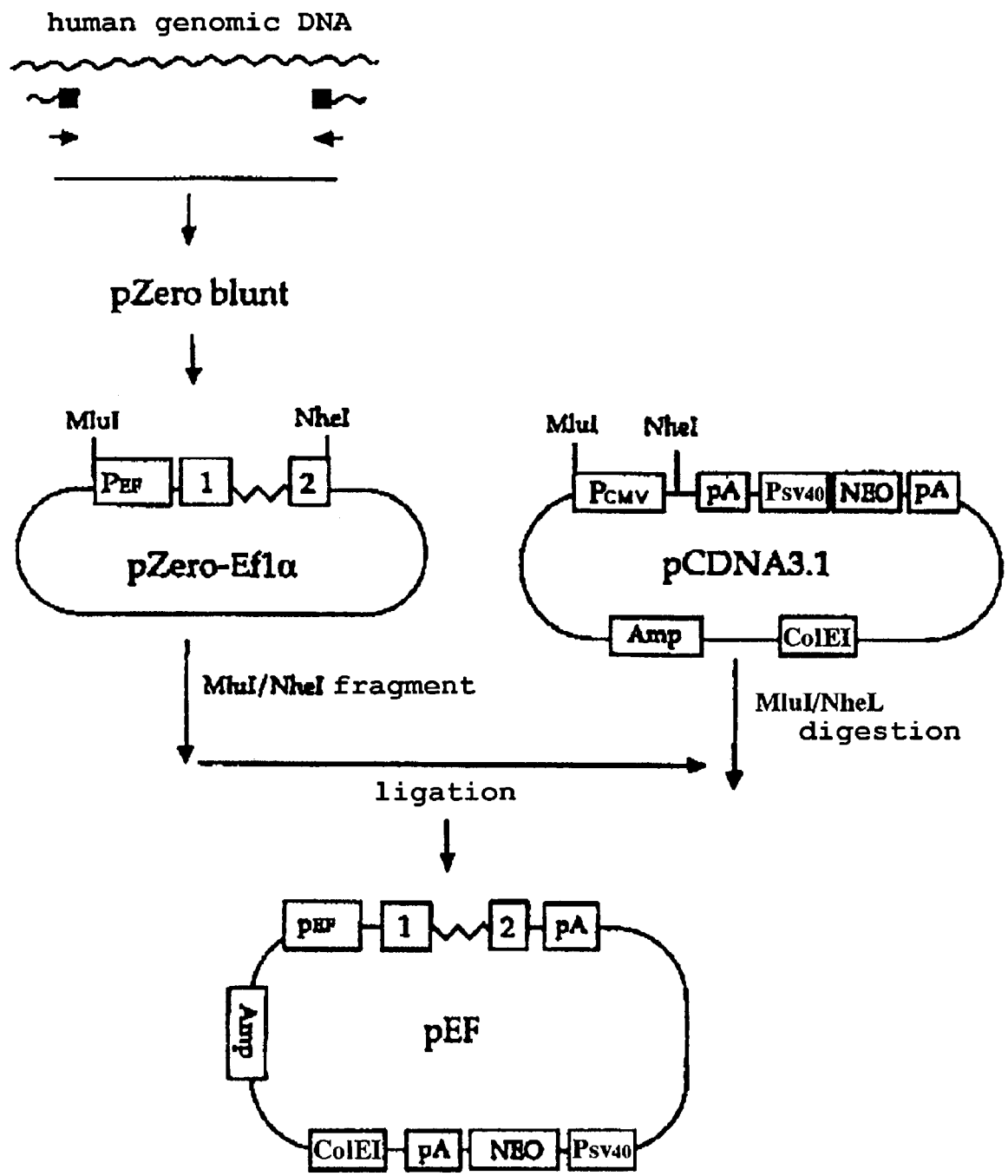
Figure 3:
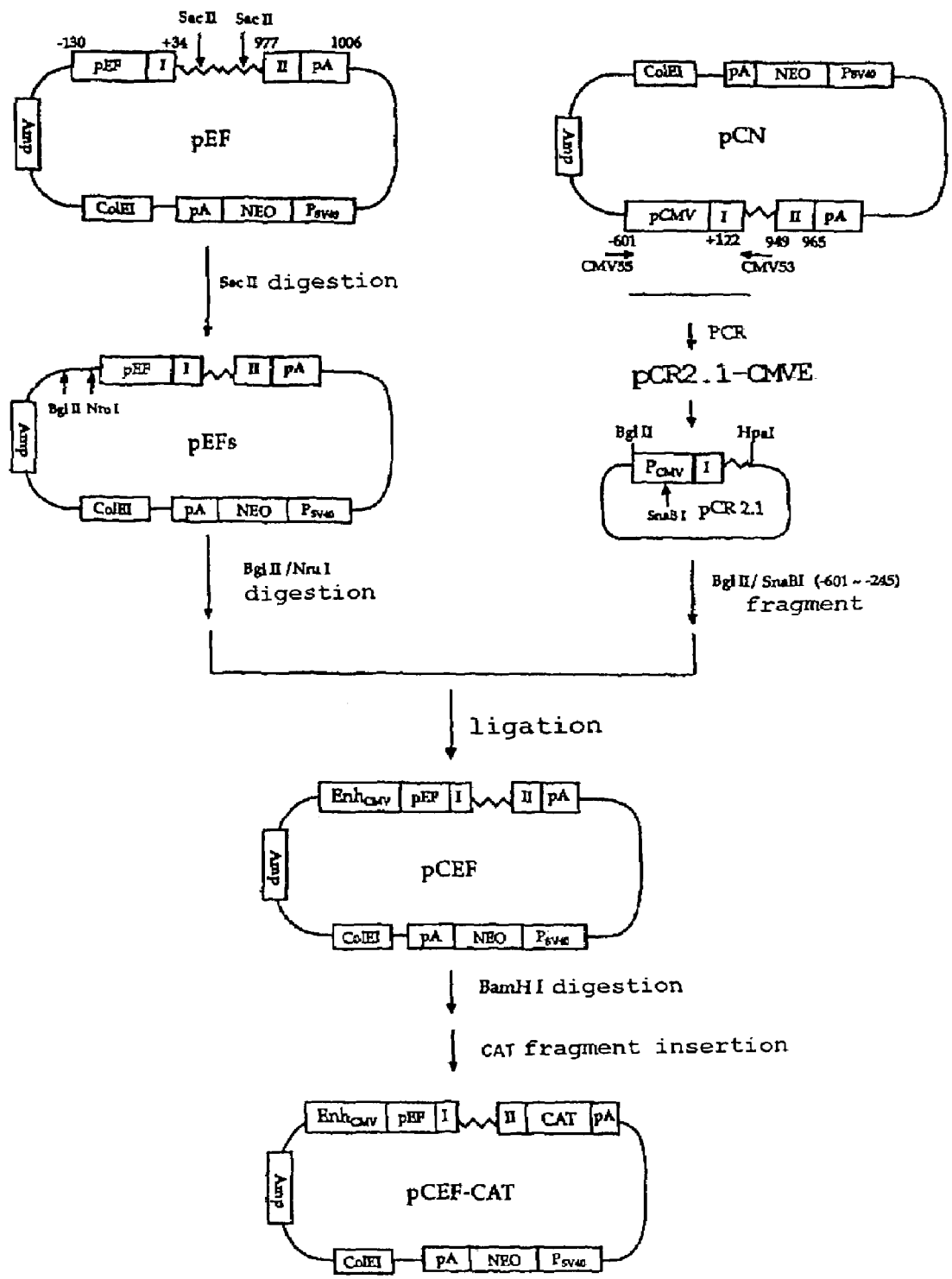
Figure 4:
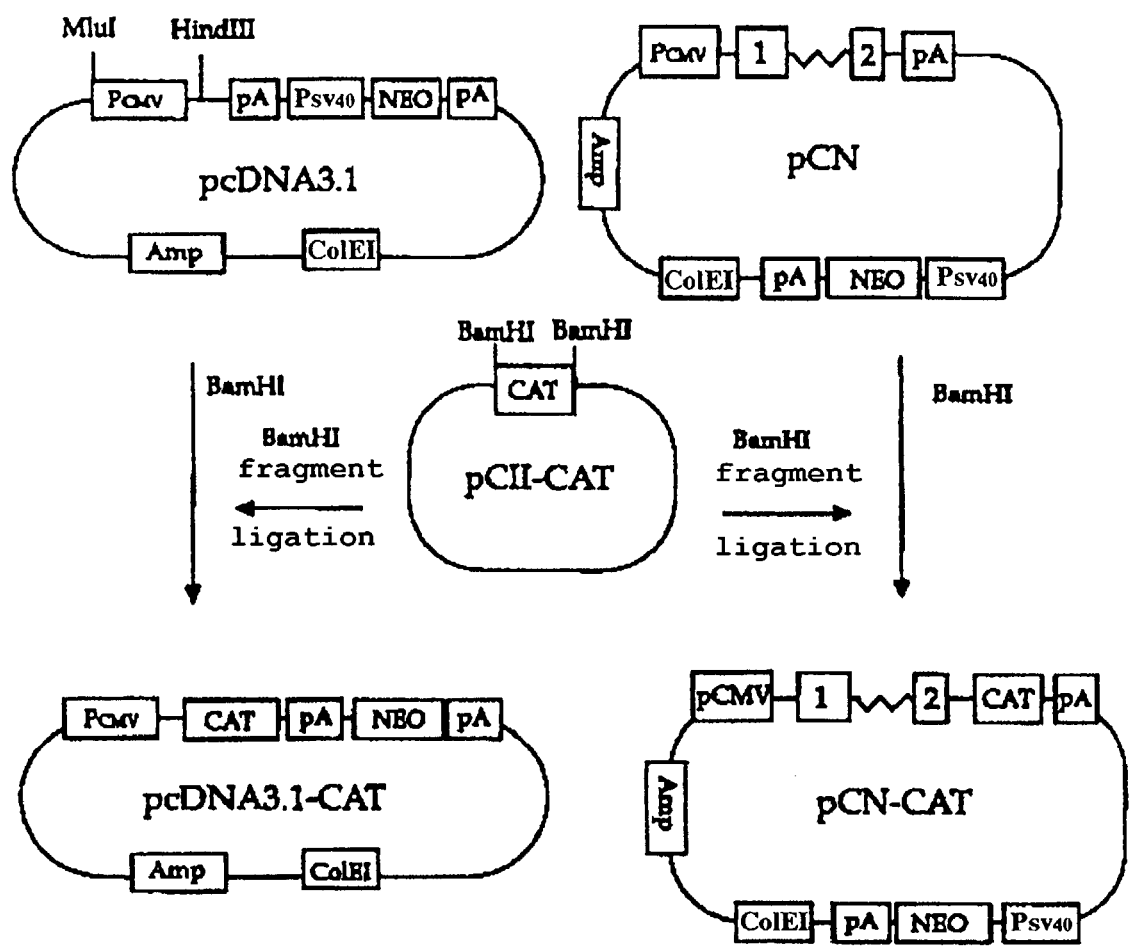
Figure 5:
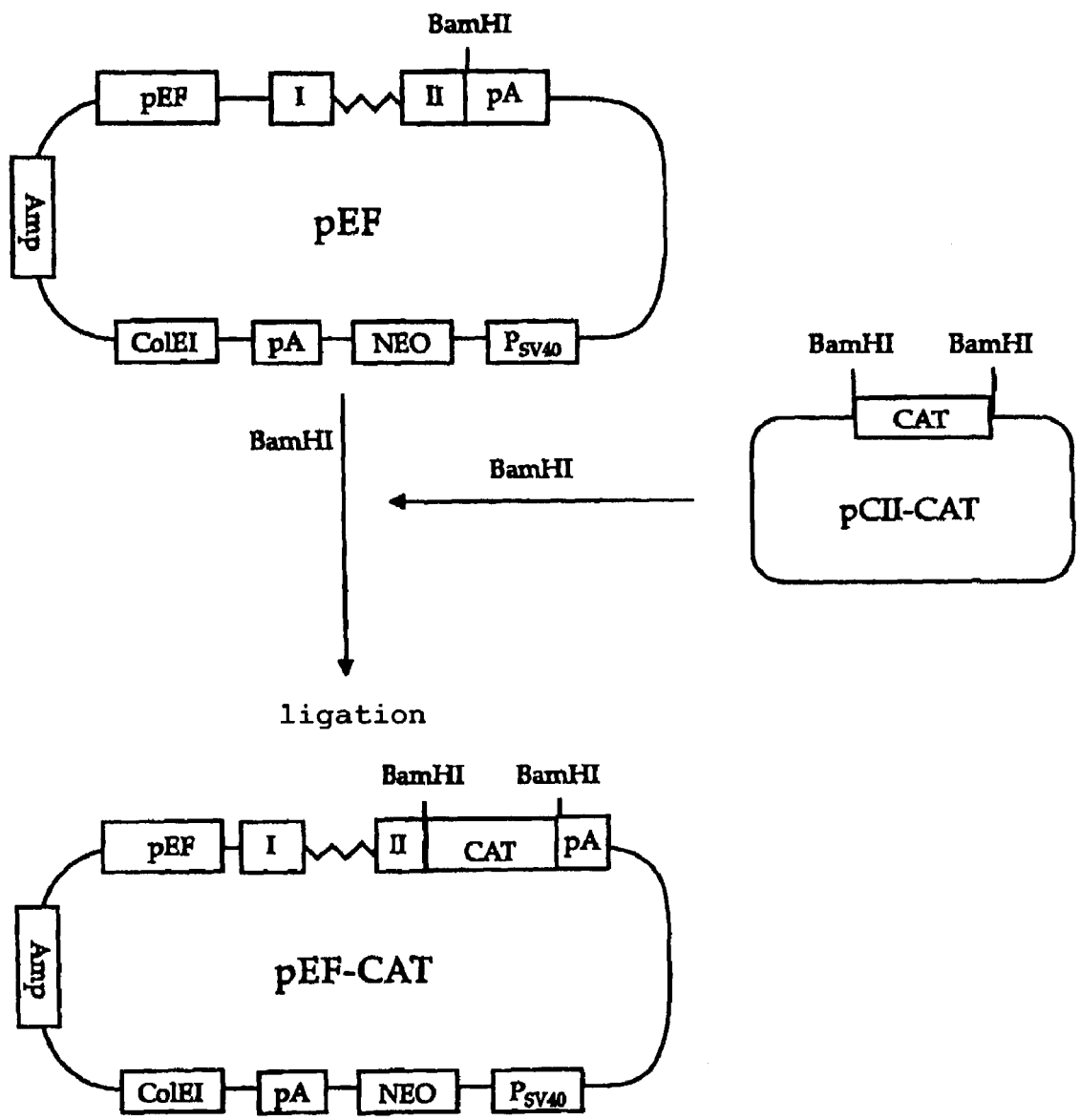
Figure 6:
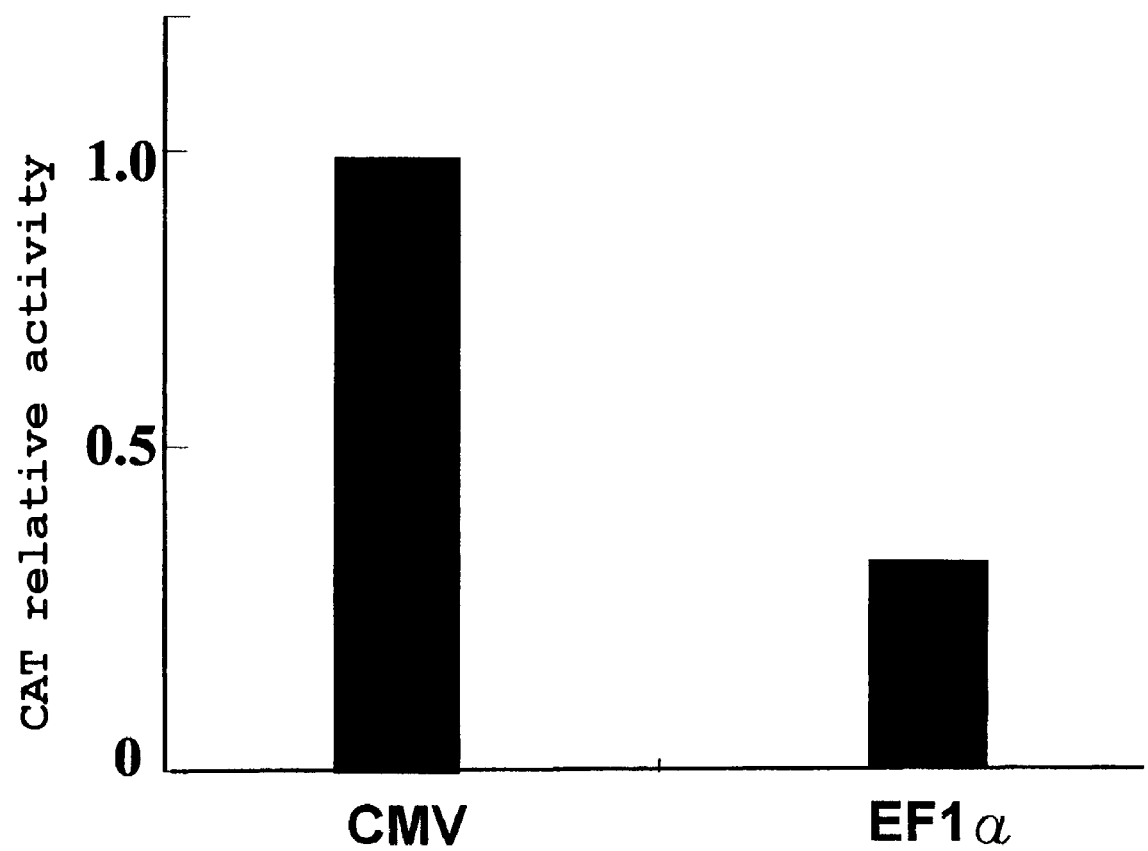
Figure 7:
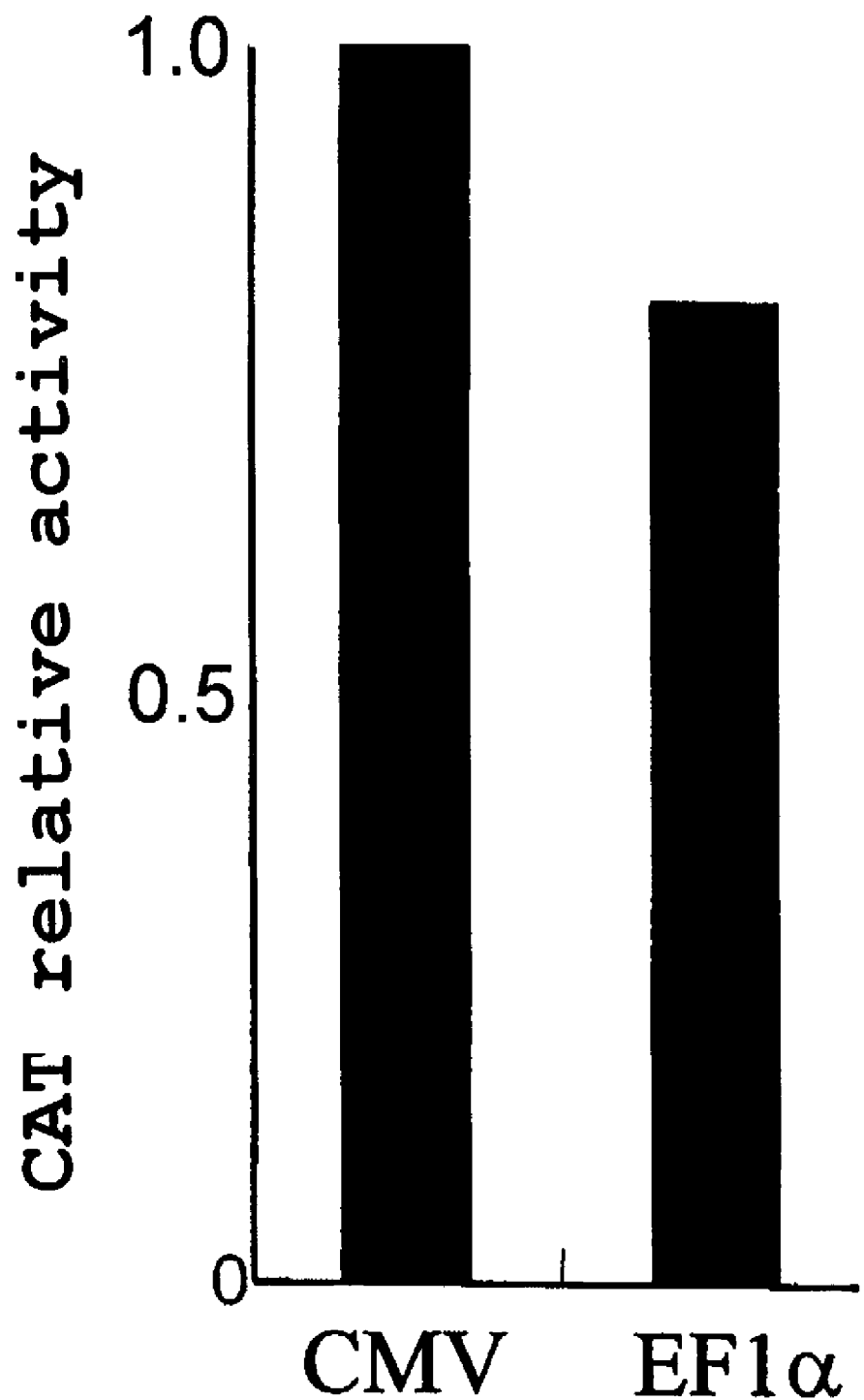
Figure 8:
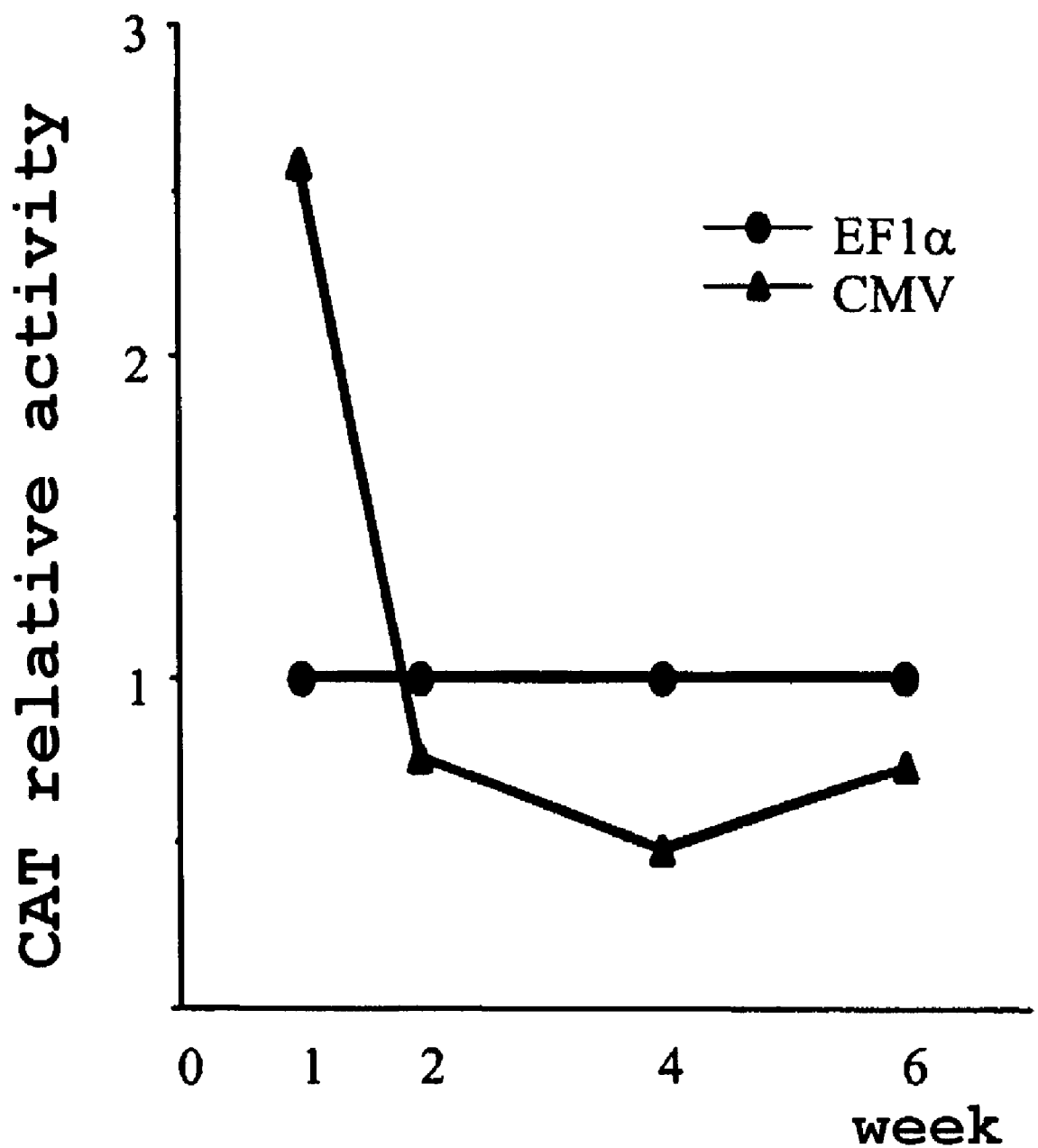
Figure 9:
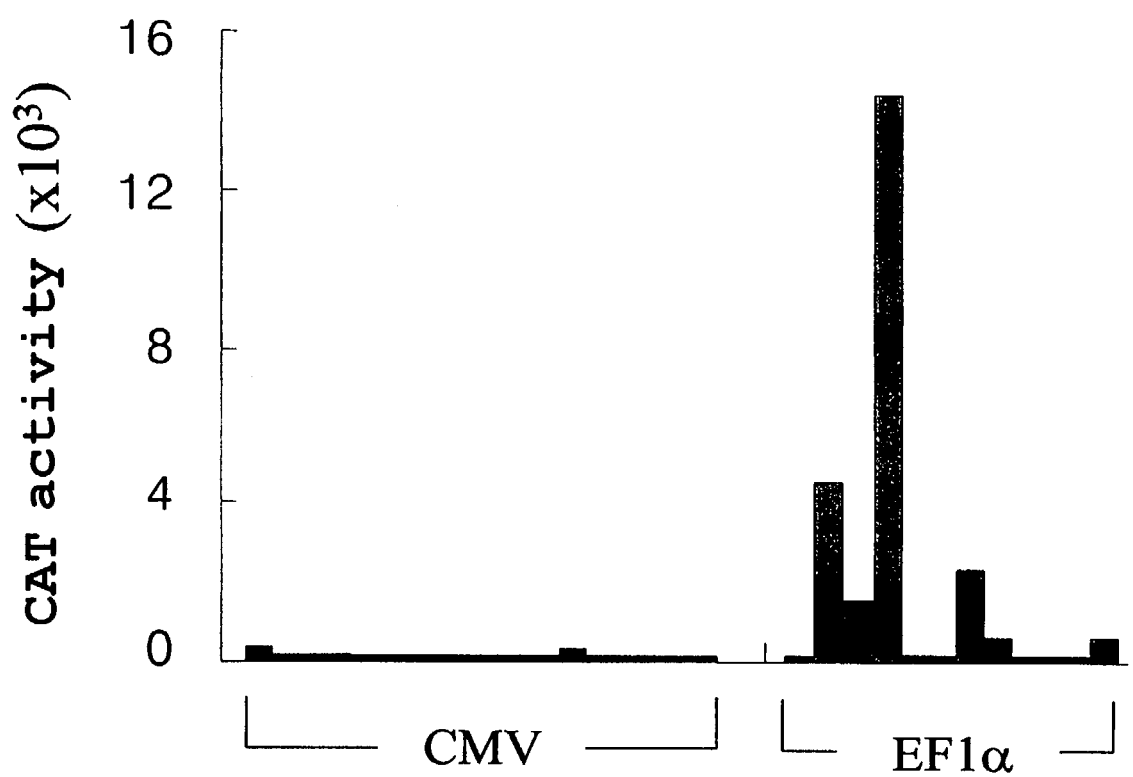
Figure 10:
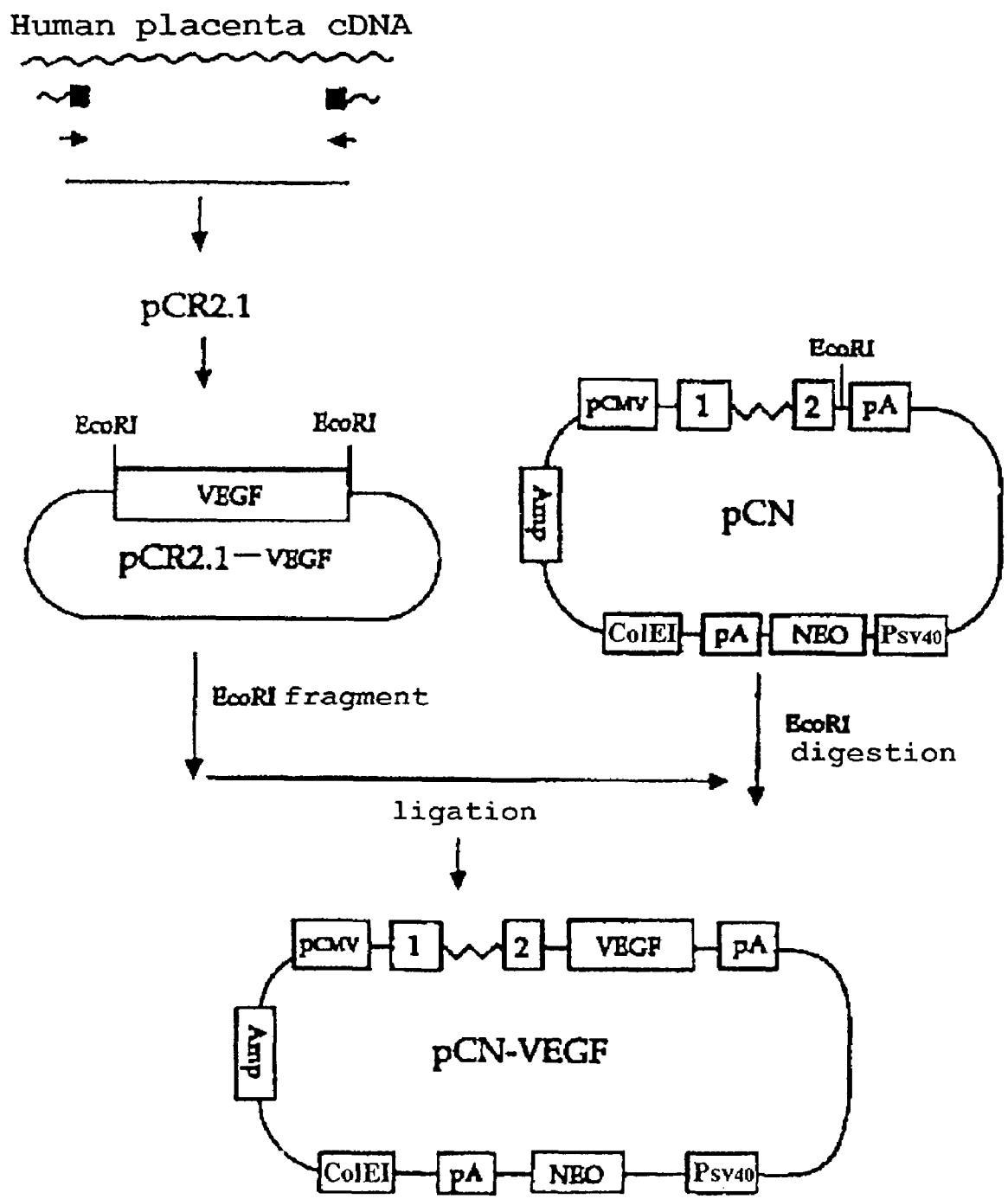
Figure 11:
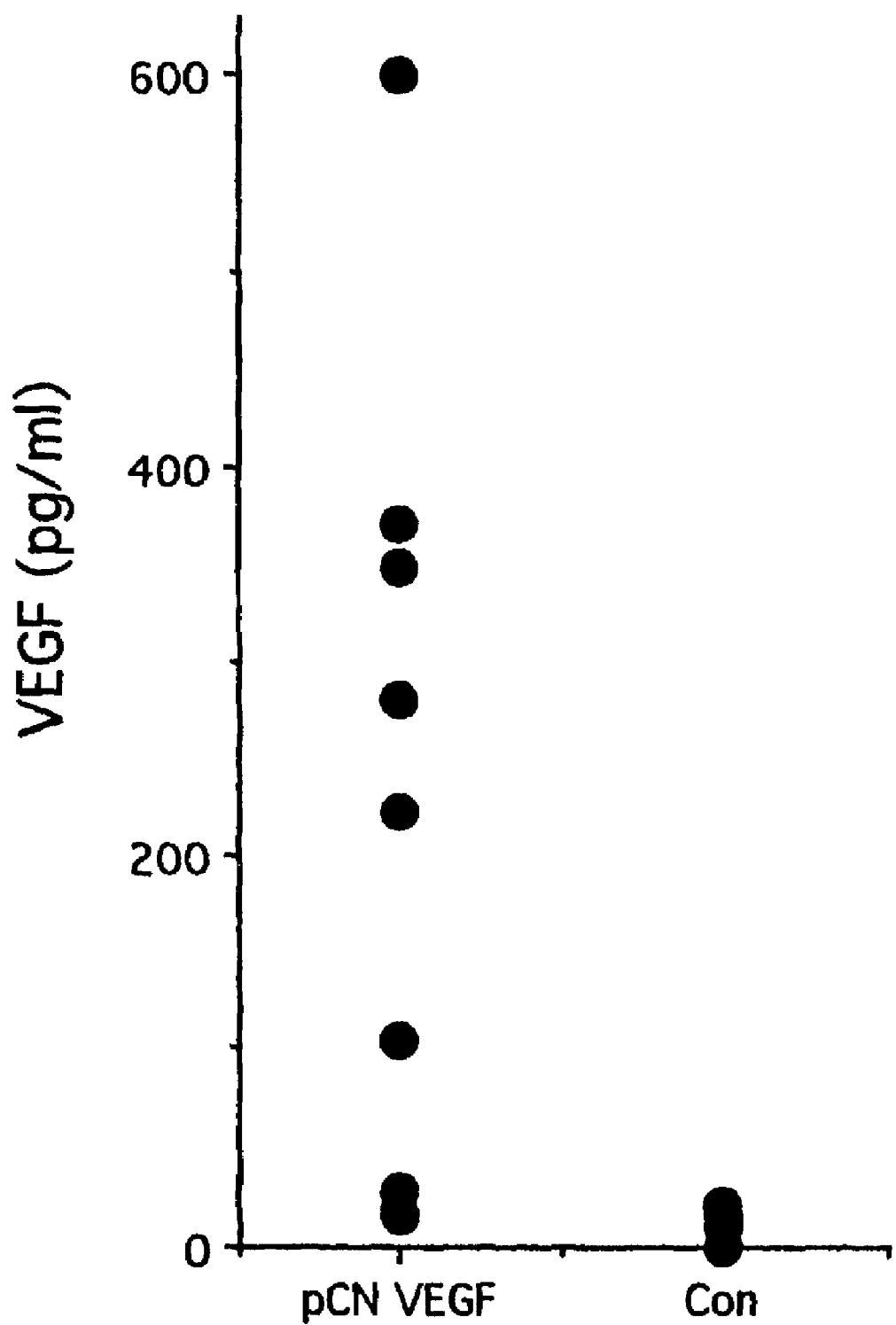
Figure 12:
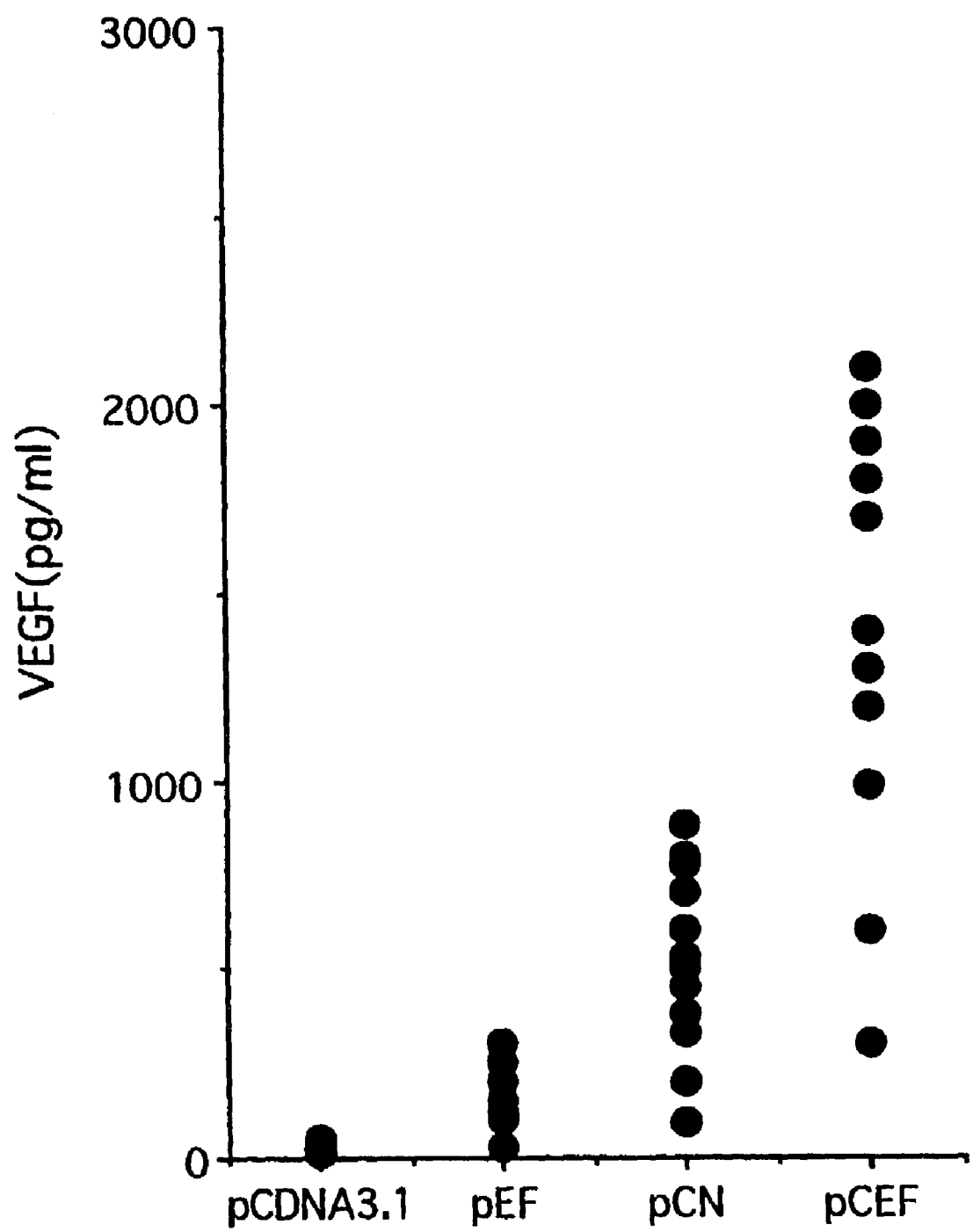
Figure 13:
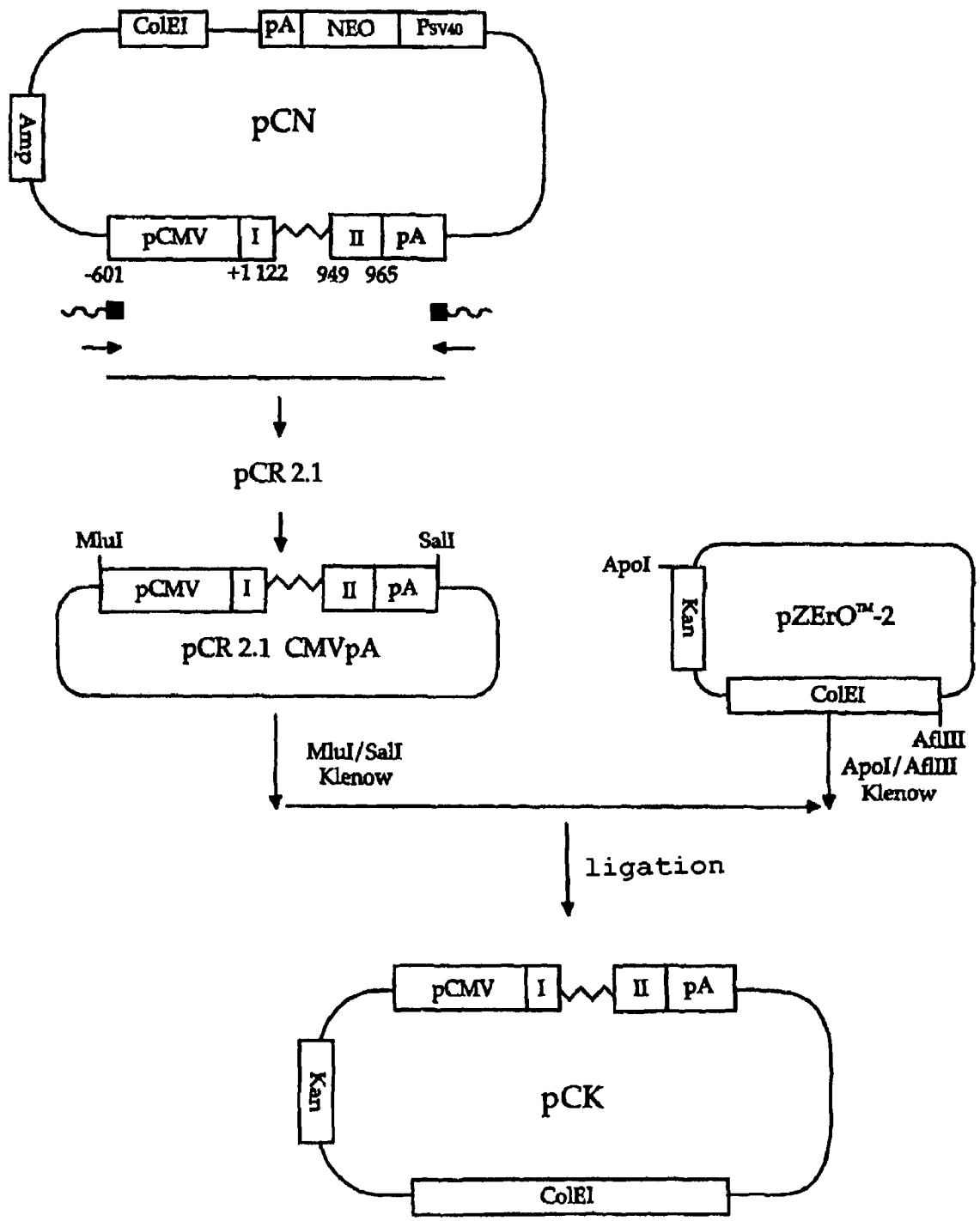
Figure 14:
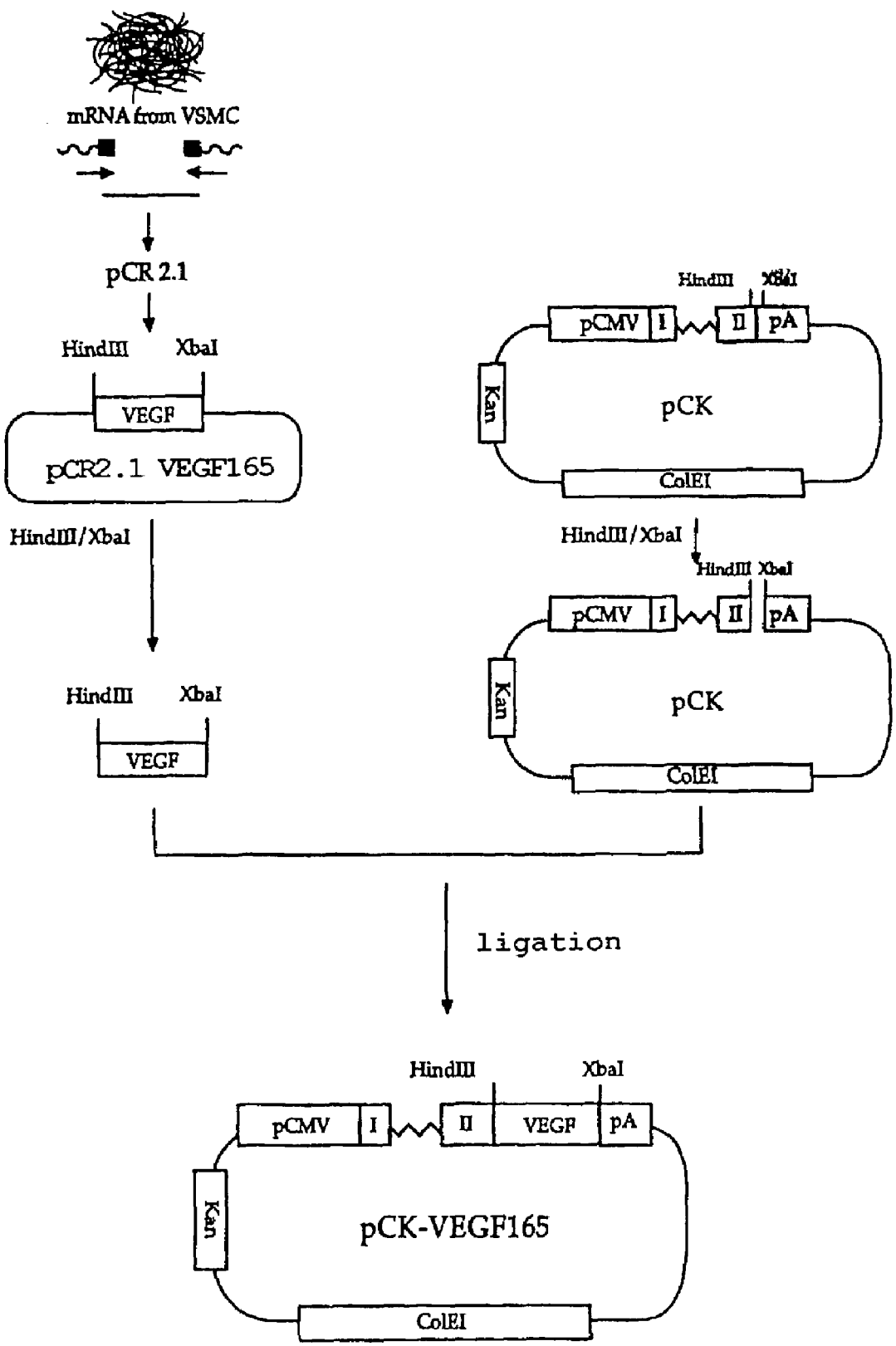
Figure 15:
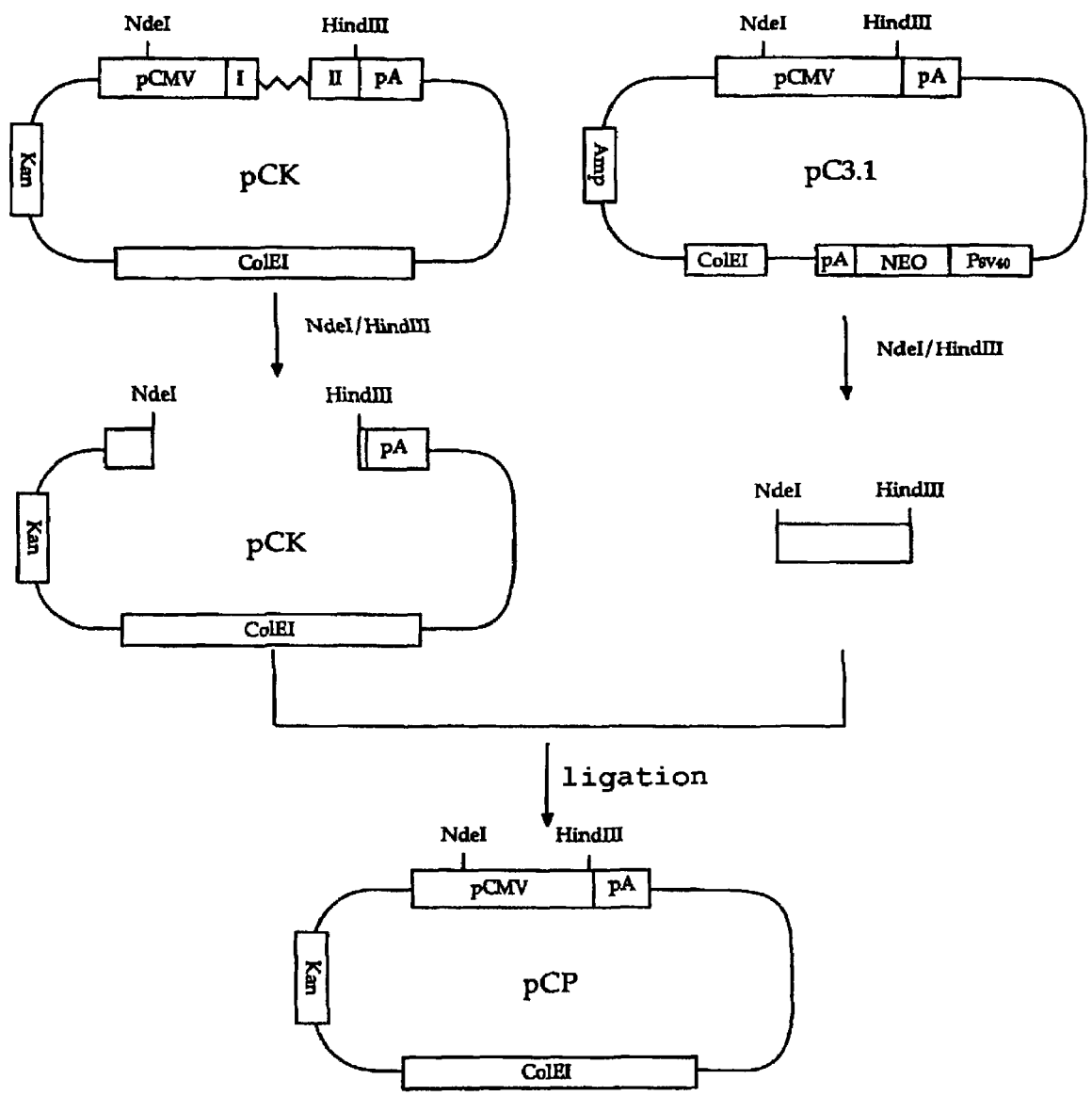
Figure 16:
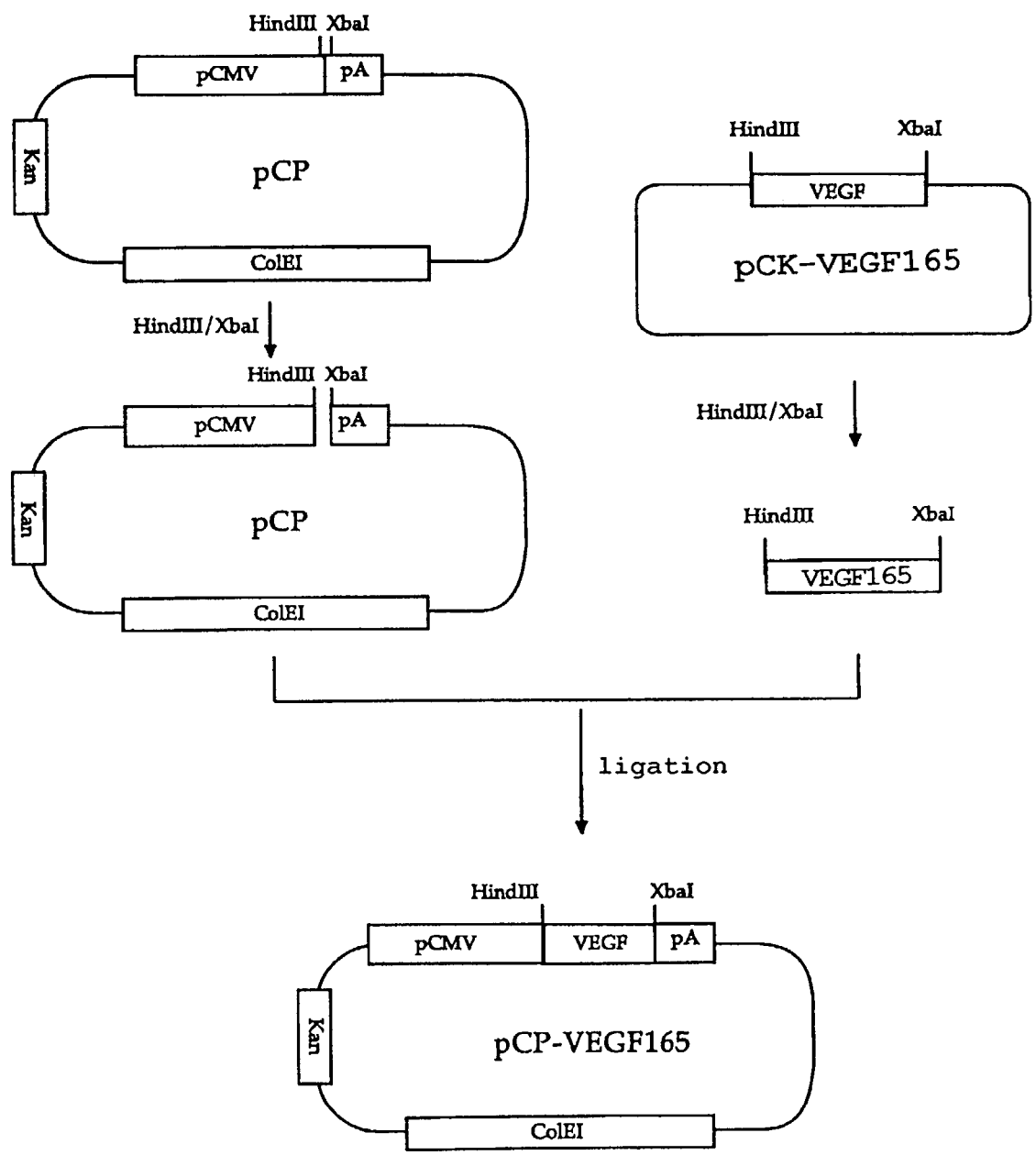
Figure 17:
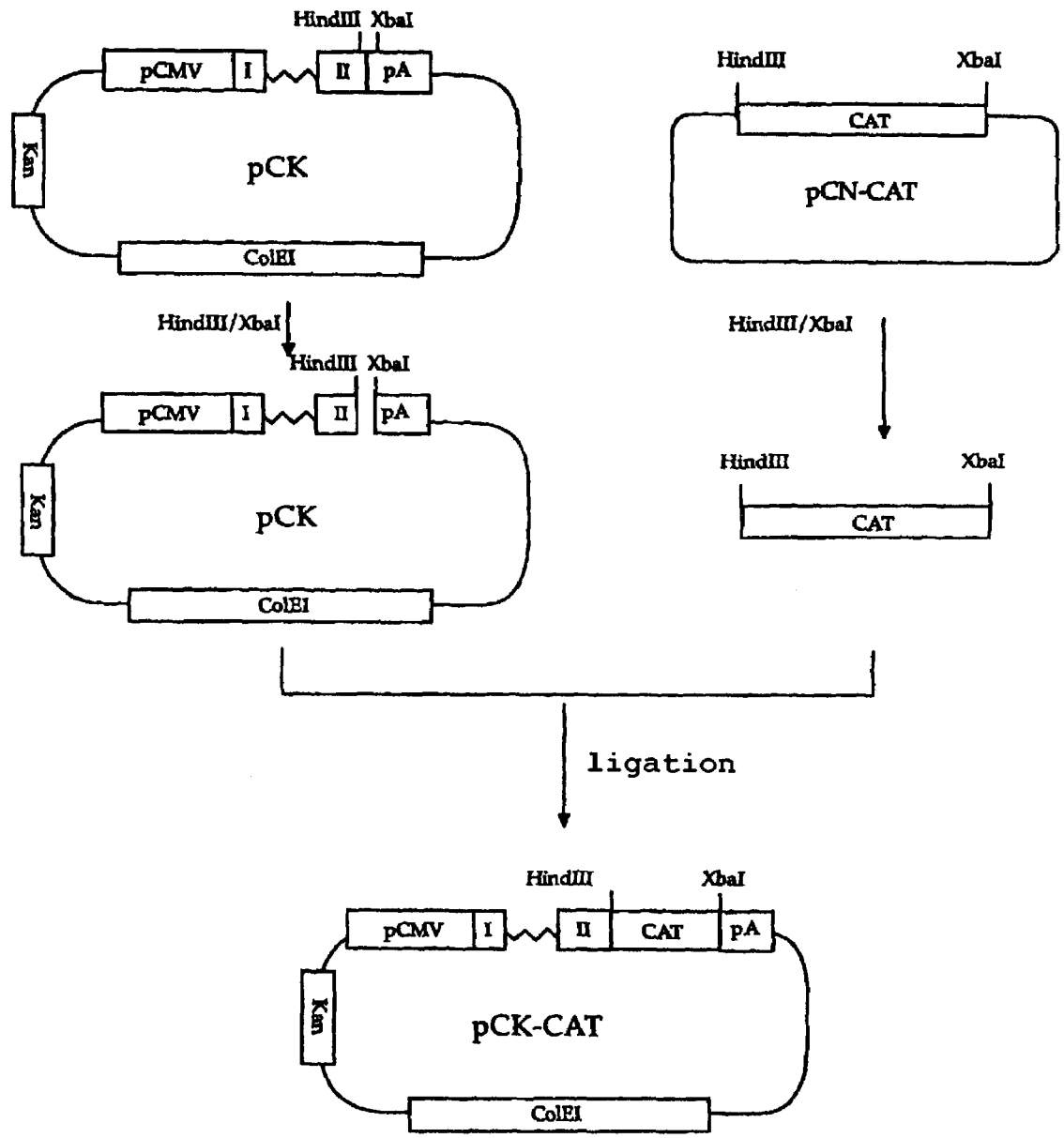
Figure 18:
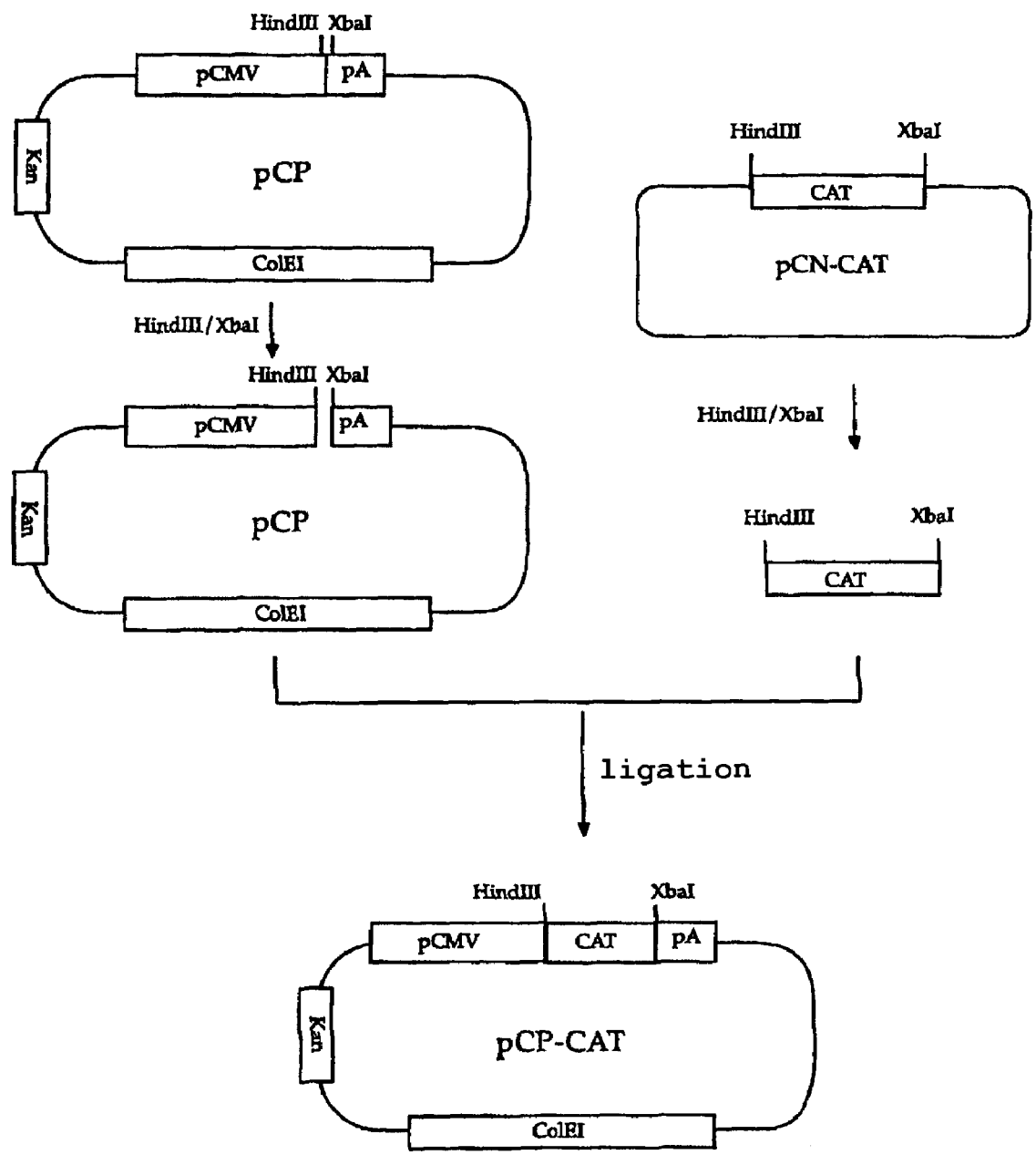
Figure 19:
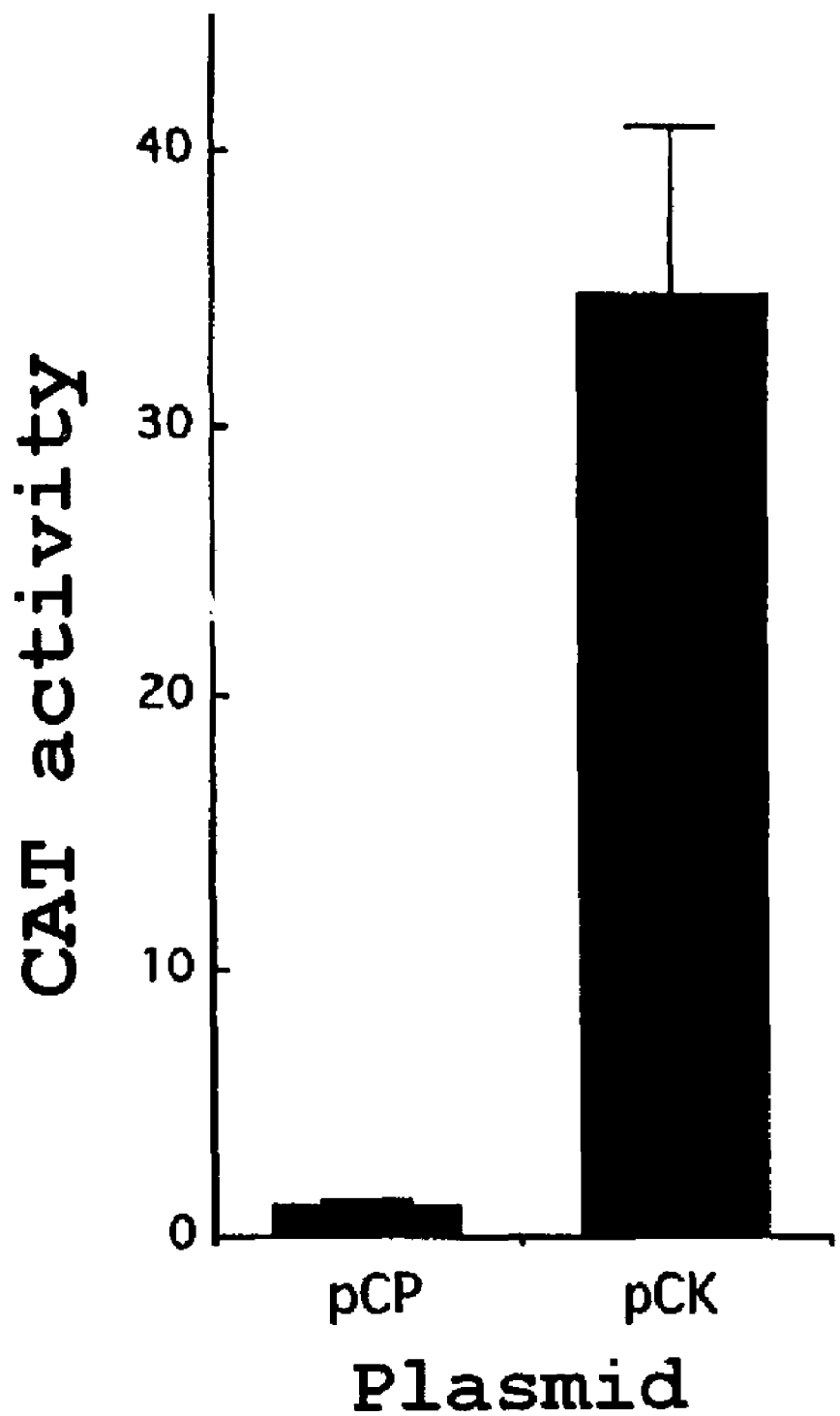
Figure 20:
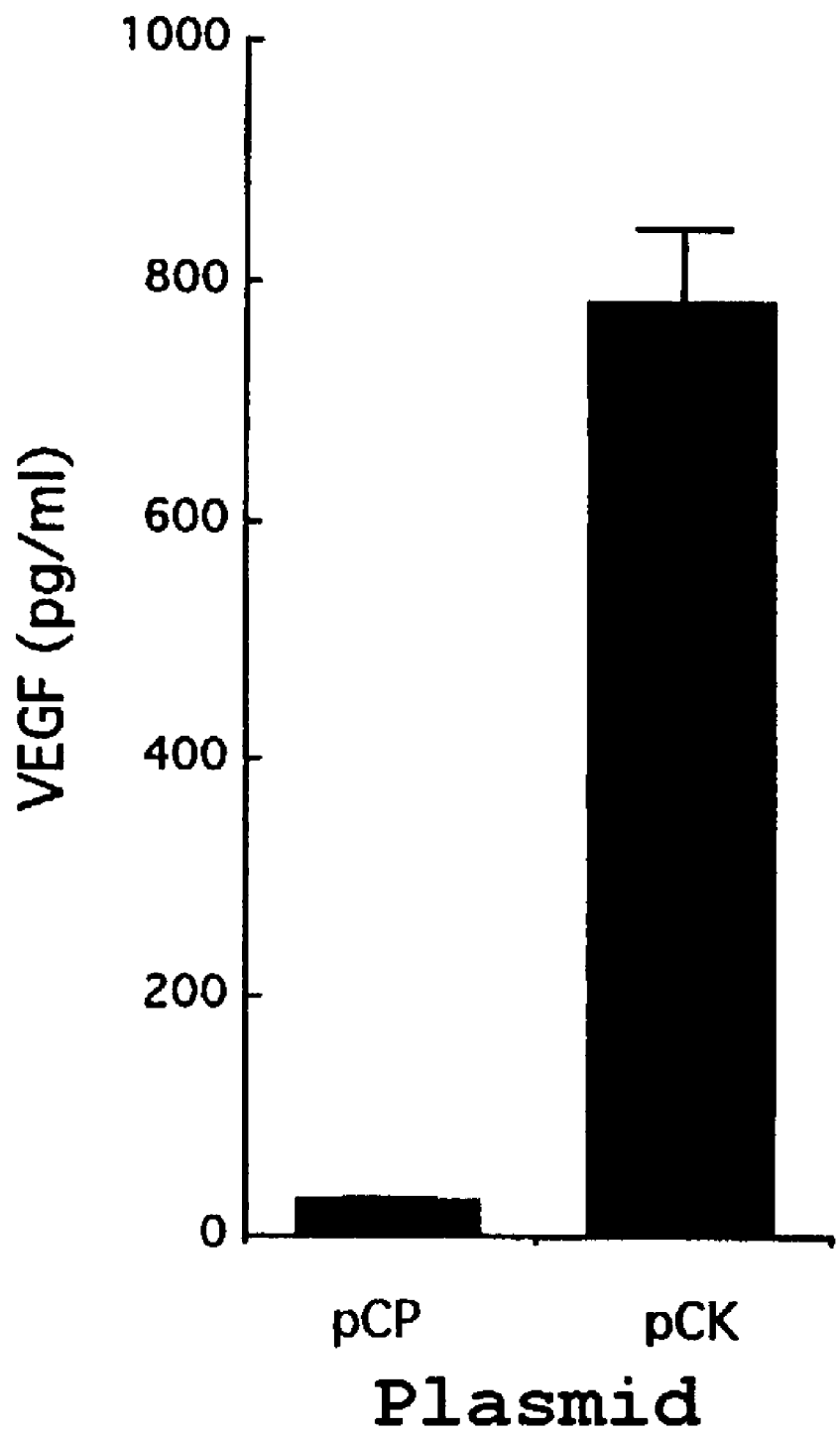
Figure 21:
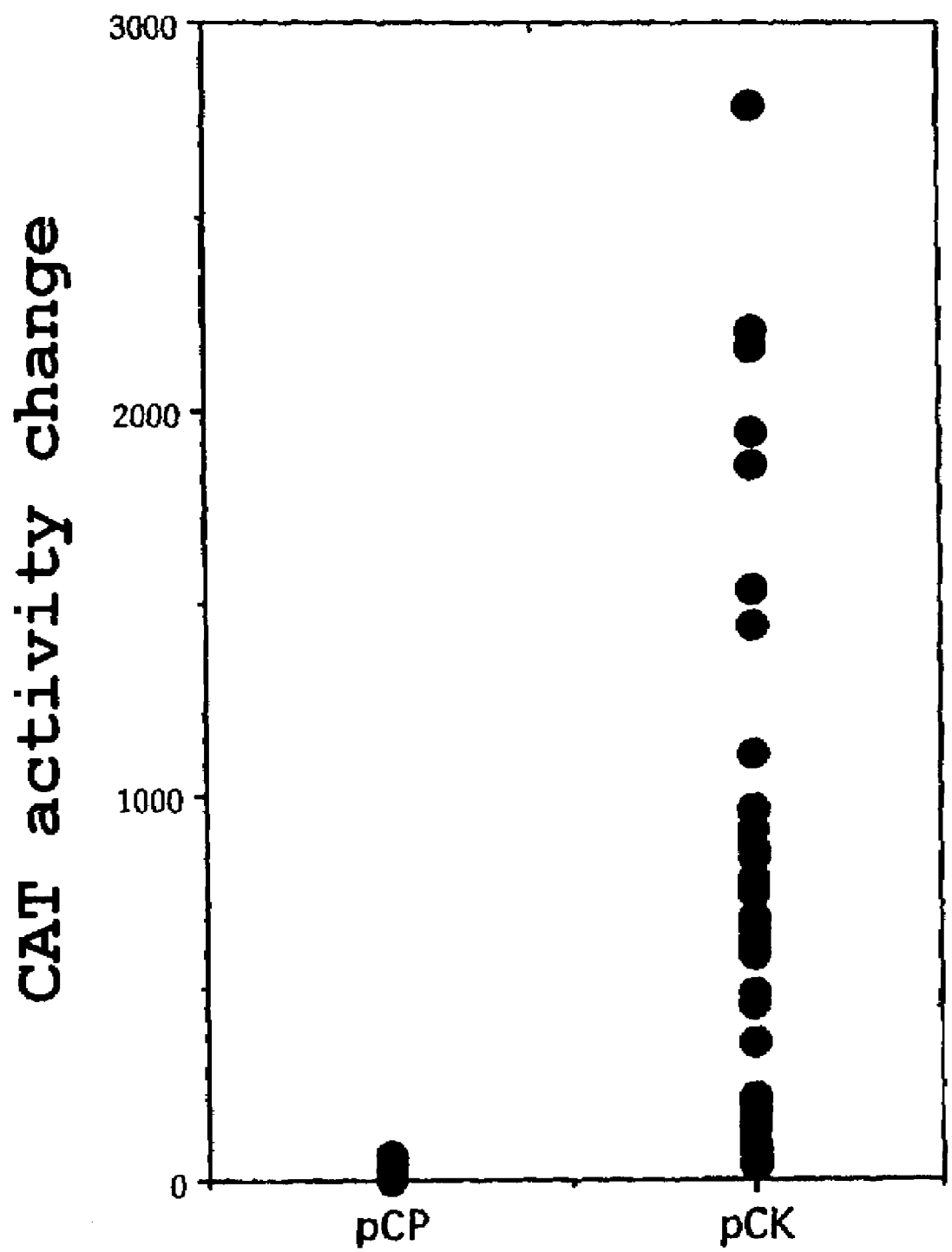
Figure 22:
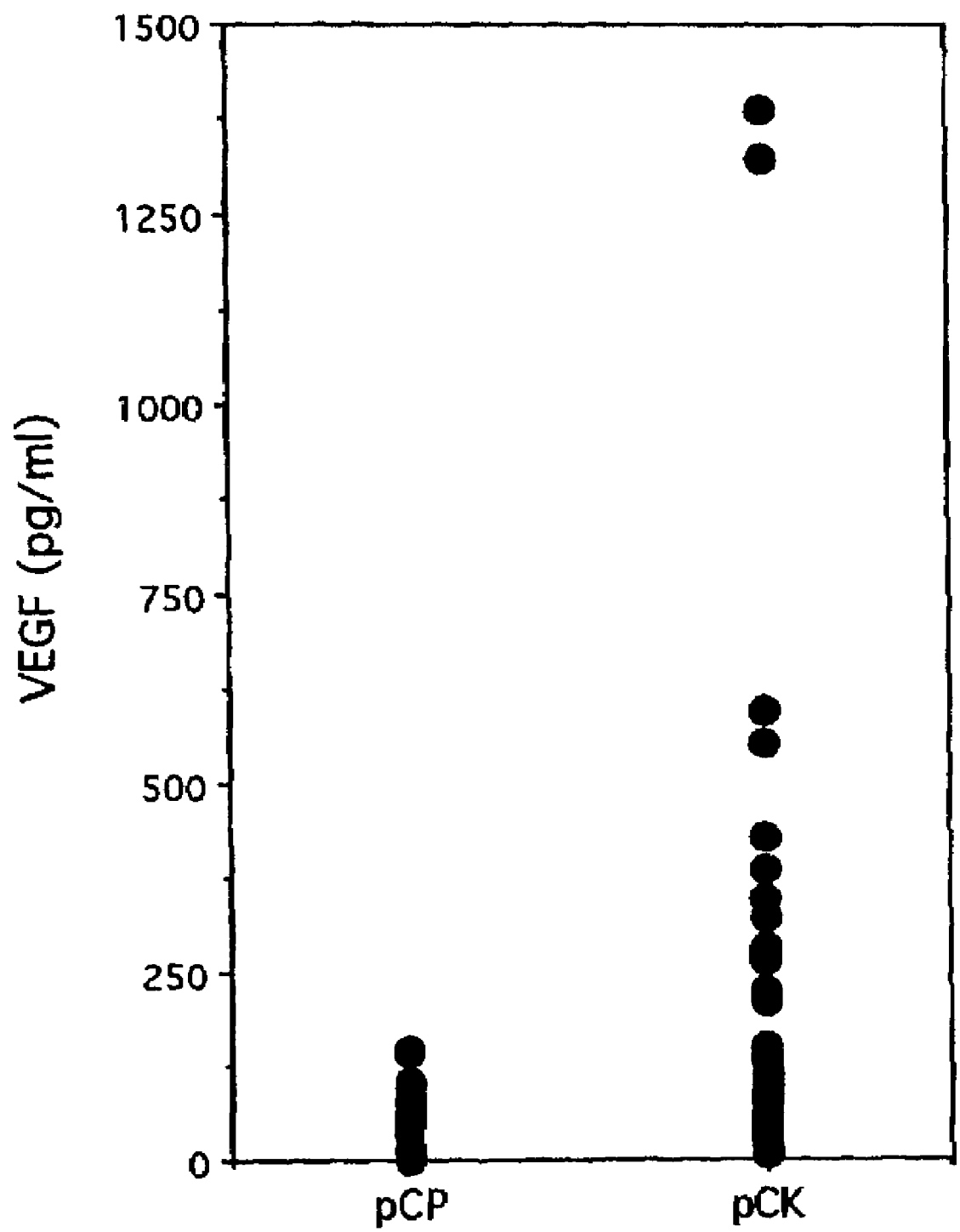
Figure 23:
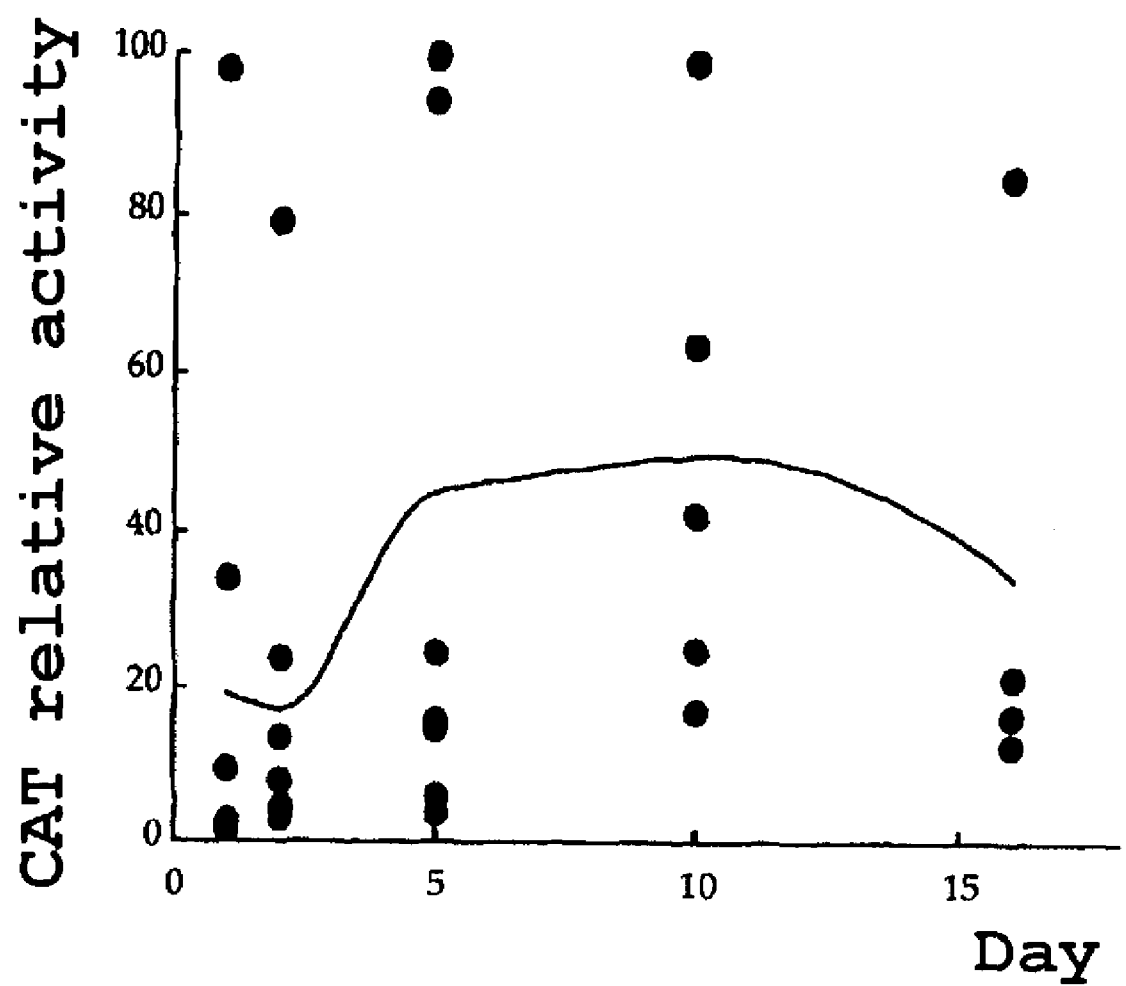
Figure 24:
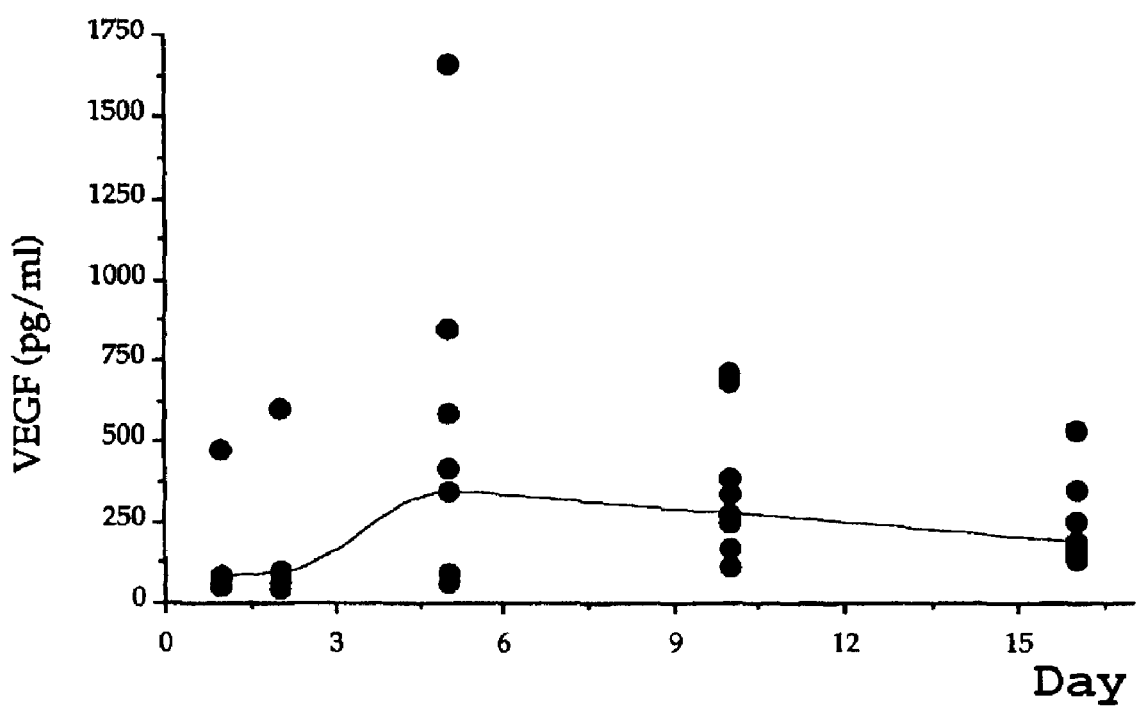
Figure 25:
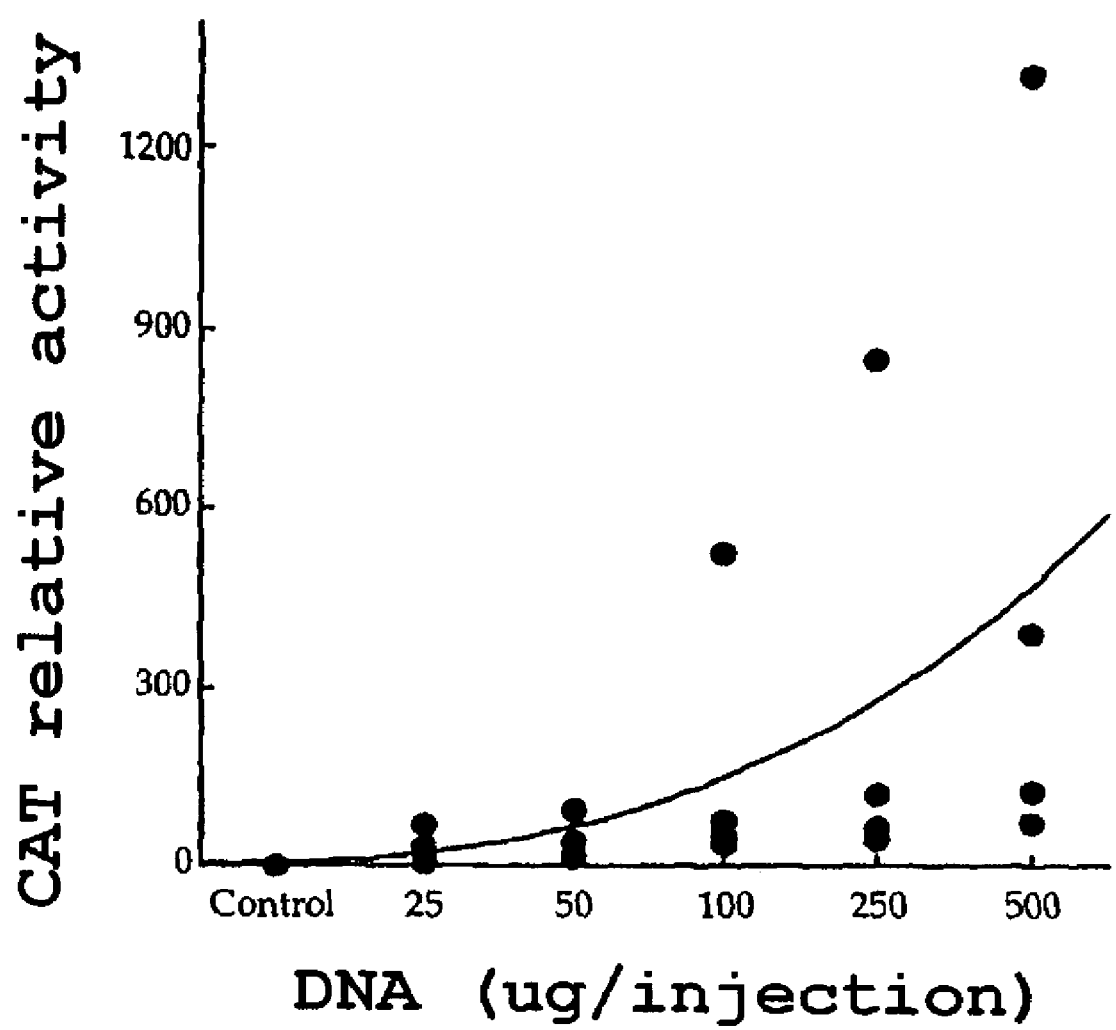
Figure 26:
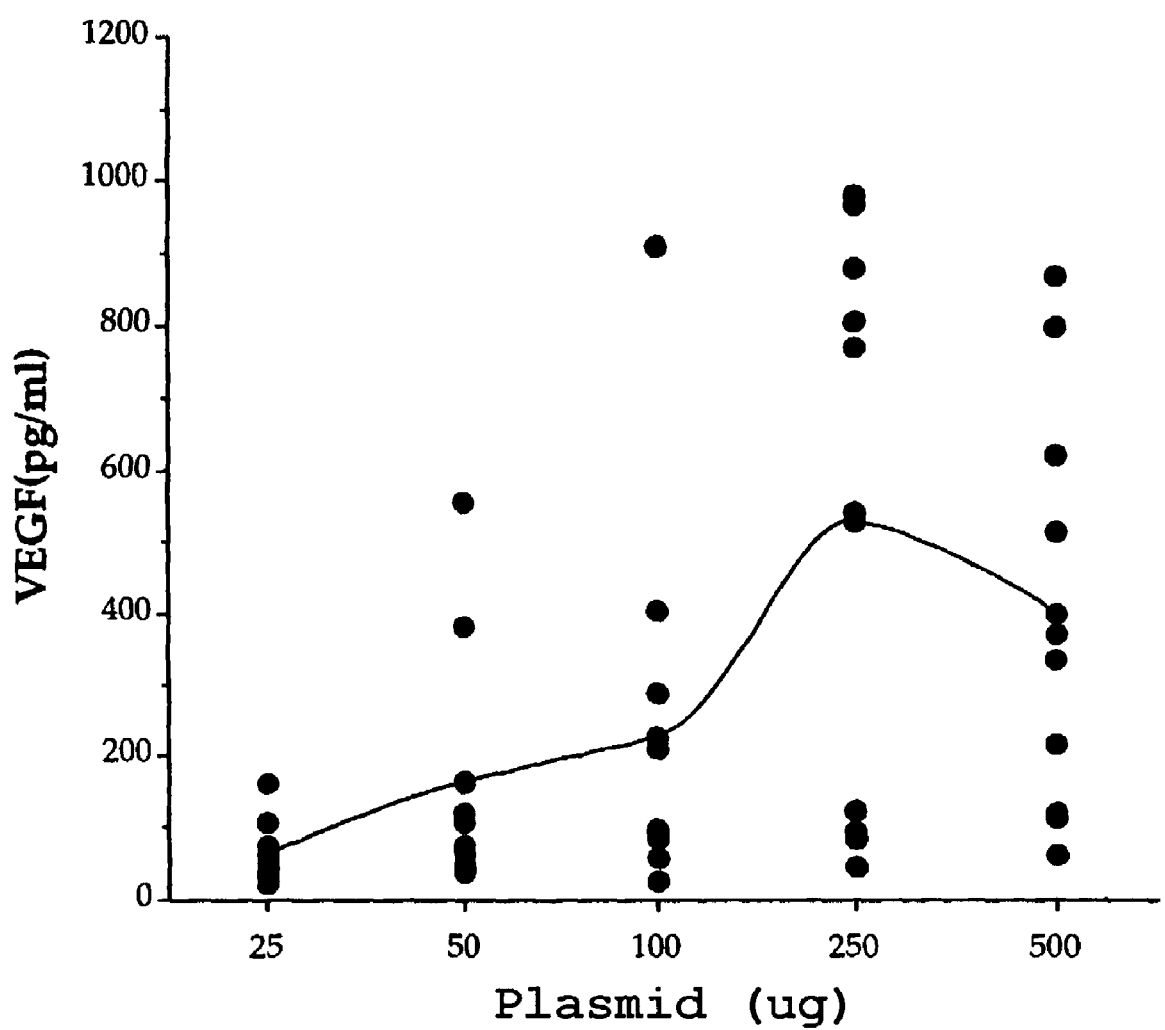
Figure 27:
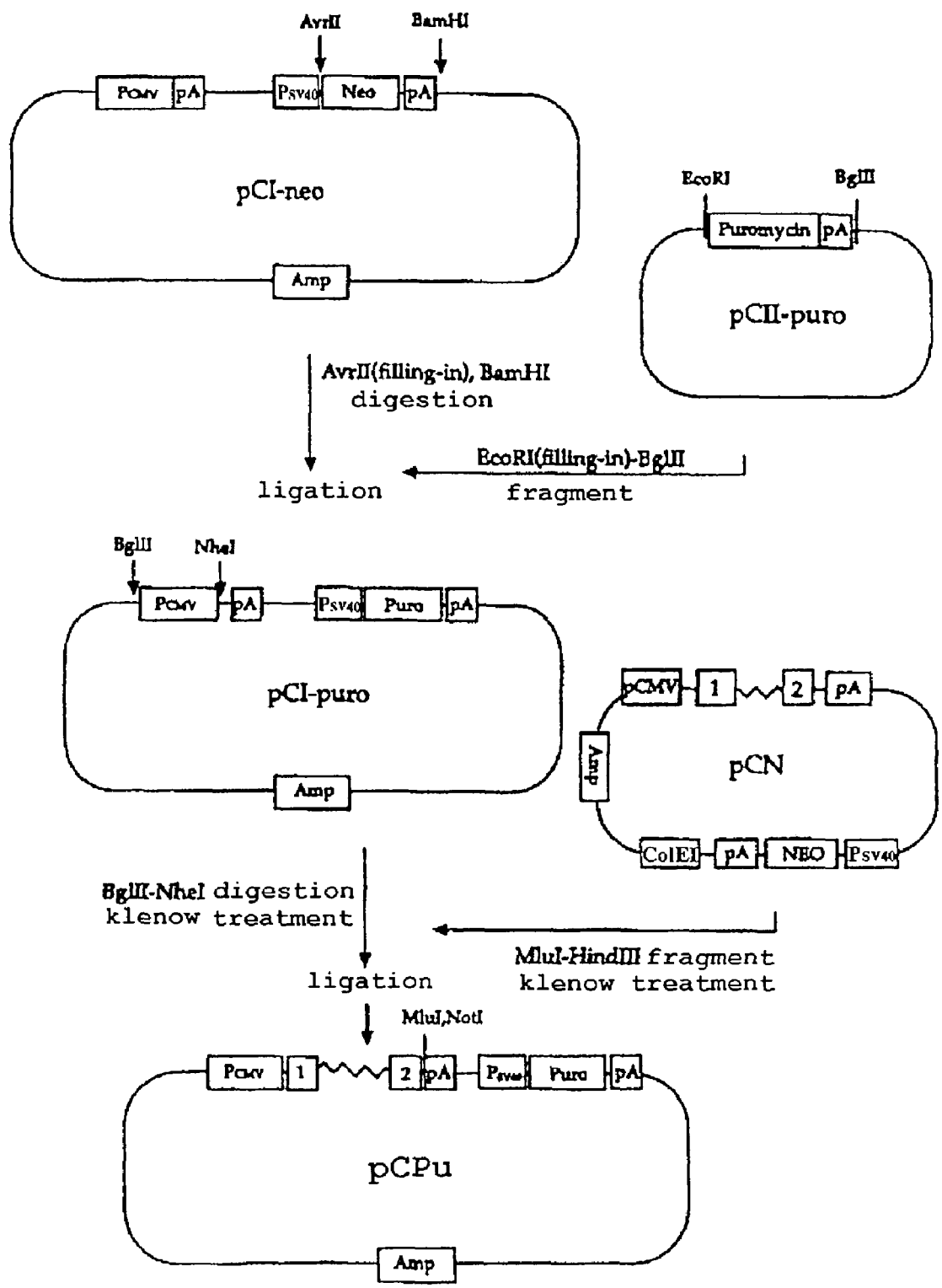
Figure 28:
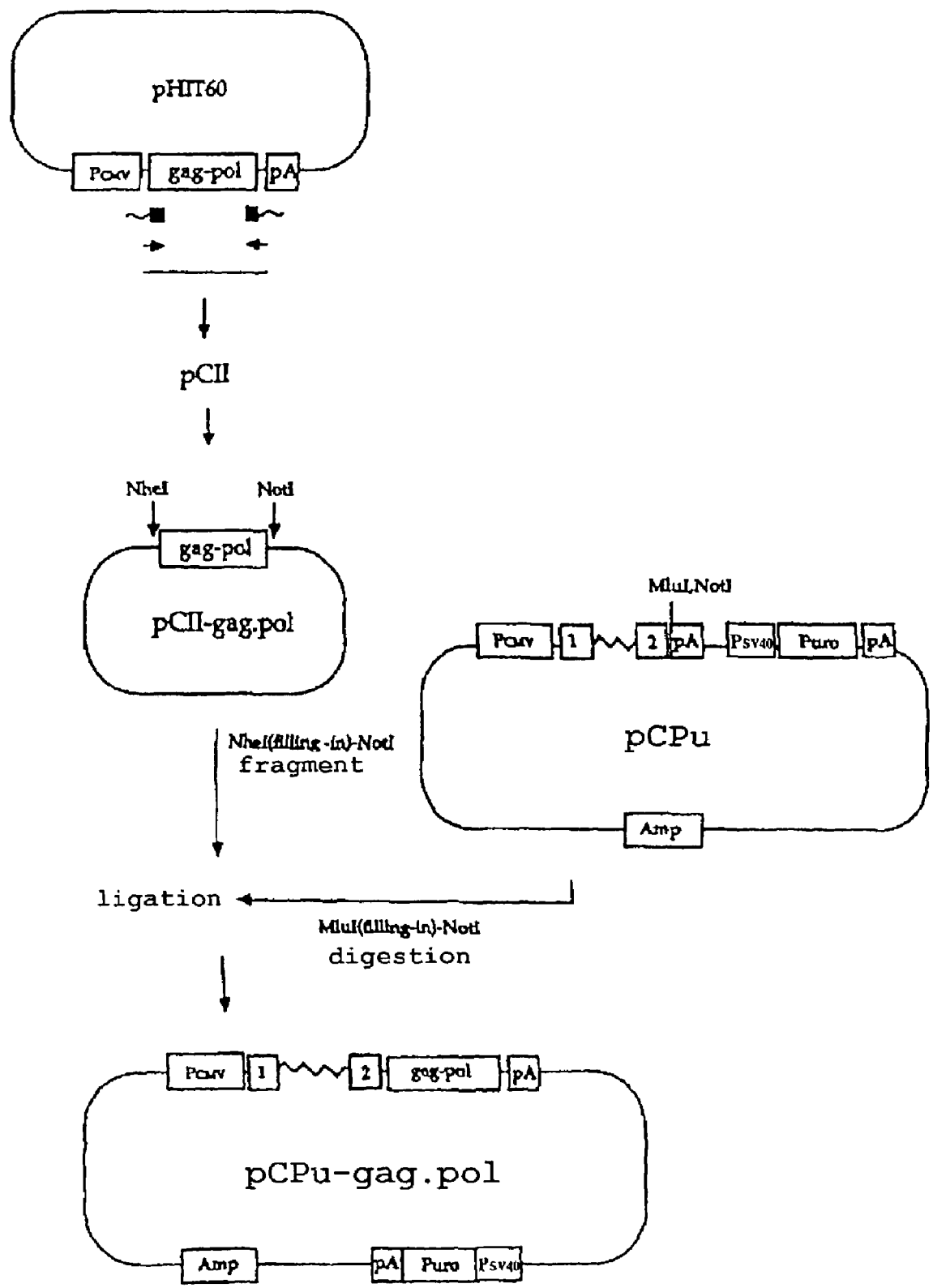
Figure 29:
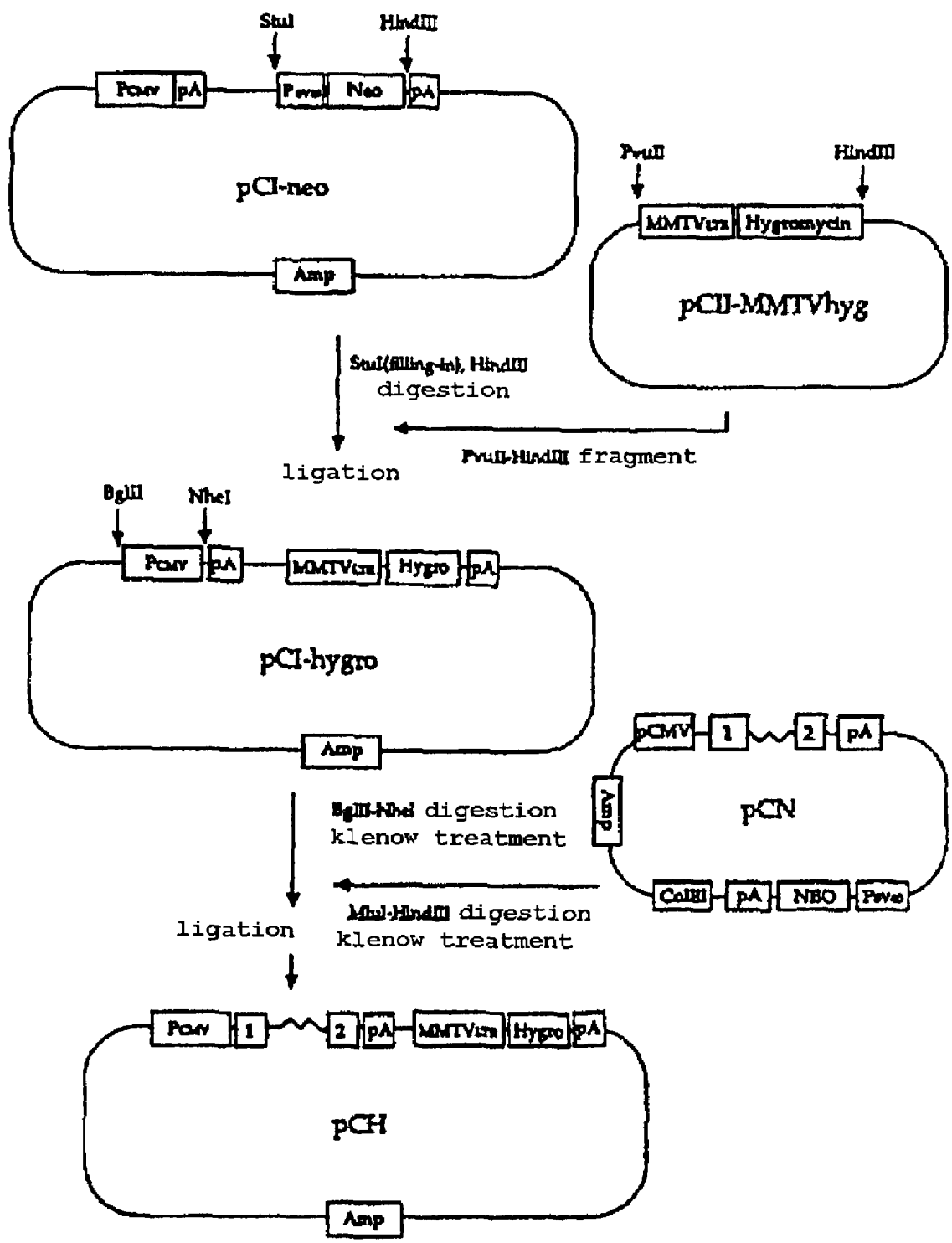
Figure 30:
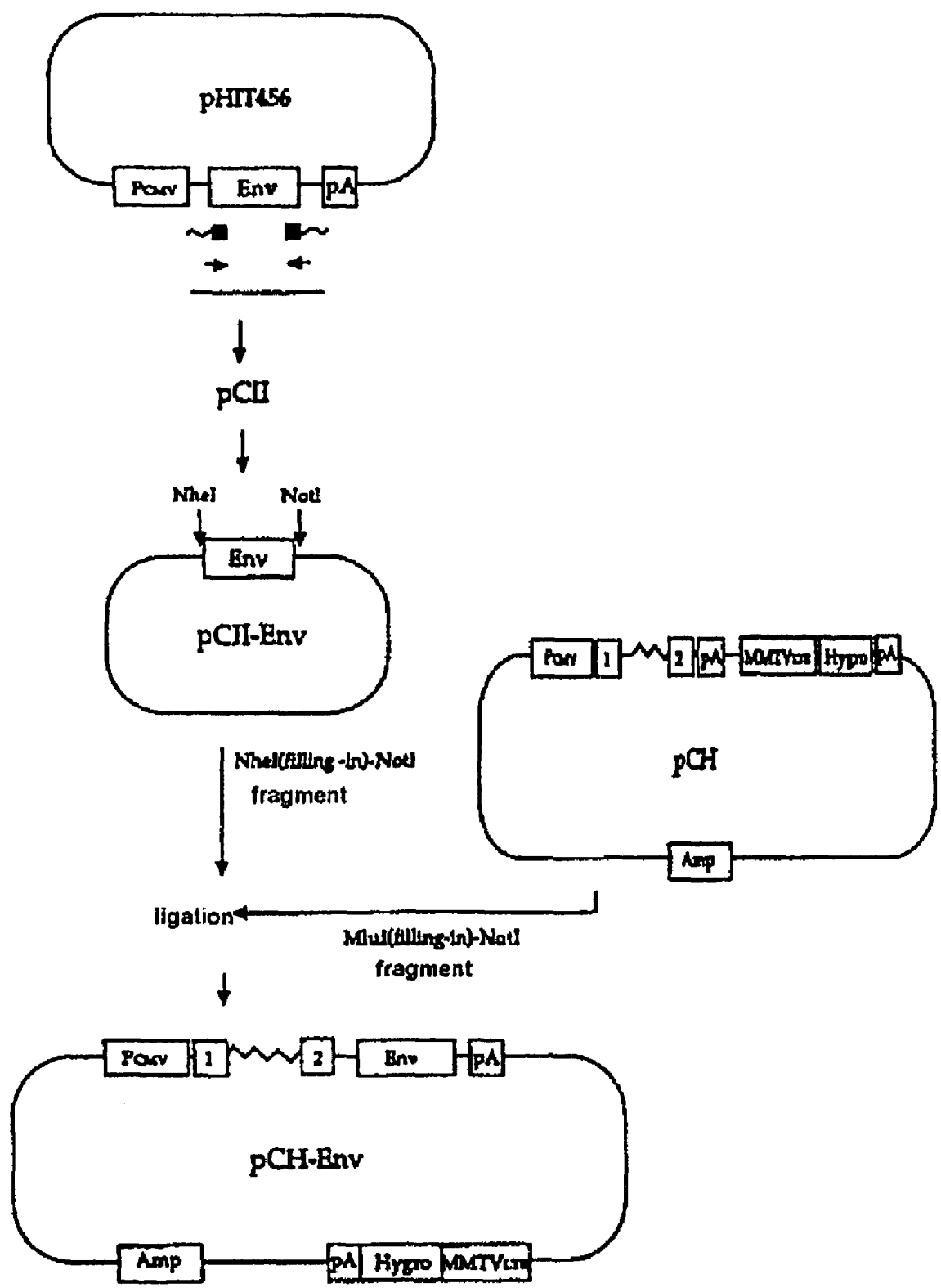

The above and other objects and features of the present invention will become apparent from the following description of the invention, when taken in conjunction with the accompanying drawings which respectively show;

FIG. 1: the procedure for constructing pCN vector,
FIG. 2: the procedure for constructing pEF vector,
FIG. 3: the procedure for constructing pCEF vector,
FIG. 4: the procedure for constructing pCDNA3.1-CAT and pCN-CAT vectors,
FIG. 5: the procedure for constructing pEF-CAT vector,
FIG. 6: the CAT activity of HeLa cells transfected with pEF-CAT or pCN-CAT vector in a transient expression system,
FIG. 7: the CAT activity of HeLa cells transfected with pEF-CAT or pCN-CAT vector in a stable expression system,
FIG. 8: the time-dependent gene expression level in HeLa cells transfected with pEF-CAT or pCN-CAT vector in a stable expression system,
FIG. 9: the gene expression levels of subclones obtained from HeLa cells transfected with pEF-CAT or pCN-CAT vector in a stable expression system,
FIG. 10: the procedure for constructing pCN-VEGF vector,
FIG. 11: the VEGF expression level of mouse muscle cells injected with pCN-VEGF vector,
FIG. 12: the gene expression levels of pCDNA3.1-VEGF, pCN-VEGF and pCEF-VEGF vectors, respectively, in a transient expression system,
FIG. 13: the procedure for constructing pCK vector,
FIG. 14: the procedure for constructing pCK-VEGF vector,
FIG. 15: the procedure for constructing pCP vector,
FIG. 16: the procedure for constructing pCP-VEGF vector,
FIG. 17: the procedure for constructing pCK-CAT vector,
FIG. 18: the procedure for constructing pCN-CAT vector,
FIG. 19: the CAT activity of C2C12 cells transfected with pCK-VEGF or pCP-VEGF vector,
FIG. 20: the VEGF expression level of C2C12 cells transfected with pCK-VEGF or pCP-VEGF vector,
FIG. 21: the CAT activity of mouse muscle cells injected with pCK-CAT or pCP-CAT vector,
FIG. 22: the VEGF expression level of mouse muscle cells injected with pCK-VEGF or pCP-VEGF vector,
FIG. 23: the time-dependent CAT expression level in mouse muscle cells injected with pCK-CAT vector,
FIG. 24: the time-dependent VEGF expression level in mouse muscle cells injected with pCK-VEGF vector,
FIG. 25: the dose-dependent level of CAT expression in mouse muscle cells injected with pCK-CAT vector,
FIG. 26: the dose-dependent level of CAT expression in mouse muscle cells injected with pCK-VEGF vector,
FIG. 27: the procedure for constructing pCPu vector,
FIG. 28: the procedure for constructing pCPu-gag•pol vector,
FIG. 29: the procedure for constructing pCH vector,
FIG. 30: the procedure for constructing pCH-env vector.

DETAILED DESCRIPTION OF THE INVENTION

The present invention provides a eukaryotic expression vector containing a multi-cloning site, a poly A signal, a selectable marker gene, a ColE1 origin of replication and a transcription regulatory element comprised of a promoter/ enhancer and the nucleotide sequence upstream of the translation initiation codon derived from HCMV IE gene or human EF1α gene. In the eukaryotic expression vector of the present invention, it is preferable that the translation regulatory element is inserted at a site upstream of said multi-cloning site, which leads to express a foreign gene from a spliced messenger RNA.

The present invention, in particular, provides a eukaryotic expression vector which comprises a promoter/enhancer and the nucleotide sequence upstream of the translation initiation codon of the HCMV IE gene as a transcription regulatory element, wherein said nucleotide sequence upstream of the translation initiation codon of the HCMV IE gene comprises the entire exon 1 sequence, the entire intron A sequence and the entire 5' untranslated region (5' UTR) of exon 2 derived from the HCMV IE gene. The vector provided by the present invention could drive higher level of gene expression, as compared with the vector containing the intron A sequence of HCMV IE gene but lacking 9 bp of the 5'UTR of exon 2 which is described in the previous report by Chapman et al. (*Nucl. Acids Res.* 19:3979-3986, 1991).

In one preferred embodiment, the present invention provides a vector designated pCN which comprises the transcription regulatory element having the nucleotide sequence of SEQ ID NO: 3. This sequence comprises the promoter/enhancer, the entire exon 1 sequence, the entire intron A sequence and the nucleotide sequence just before the initiation codon ATG of exon 2 derived from the HCMV IE gene. In SEQ ID NO: 3, the nucleotide sequence from 1 to 599 corresponds to the promoter/enhancer; the nucleotide sequence from 600 to 720, to the entire exon 1 sequence; the nucleotide sequence from 721 to 1547, to the entire intron A sequence; and the nucleotide sequence from 1548 to 1564, to the nucleotide sequence just before the initiation codon ATG of exon 2 of the HCMV IE gene.

It has been confirmed that the eukaryotic expression vector pCN comprising the transcription regulatory element derived from the HCMV IE gene can drive effective foreign gene expression and virus packaging (see Examples 4 and 17)

The present invention also provides a eukaryotic expression vector which comprises a promoter/enhancer and the nucleotide sequence upstream of the translation initiation codon of the human EF1α gene as a transcription regulatory element, wherein said nucleotide sequence upstream of the translation initiation codon of the human EF1α gene comprises the entire exon 1 sequence, the entire intron A sequence and the entire 5'UTR of exon 2 derived from the human EF1α gene.

To complement the drawbacks of gene expression system using a viral gene derived promoter such as the HCMV IE gene-derived promoter, the present invention provides a eukaryotic expression vector designated pEF which comprises the transcription regulatory element having the nucleotide sequence of SEQ ID NO: 6. This sequence comprises the promoter/enhancer, the entire exon 1 sequence, the entire intron A sequence and the nucleotide sequence just before the initiation codon ATG of exon 2 derived from the human EF1α gene. In SEQ ID NO: 6, the nucleotide sequence from 1 to 137 corresponds to the promoter/enhancer; the nucleotide sequence 138 to 158, to the entire exon 1 sequence; the nucleotide sequence from 159 to 1104, to the entire intron A sequence; and the nucleotide sequence from 1105 to 1136, to the nucleotide sequence just before the initiation codon ATG of exon 2 of the human EF1α gene.

In terms of comparing the gene expression efficiency, the pCN vector shows a higher level of gene expression than the pEF vector in a transient expression system, whereas the pEF vector shows a higher level of gene expression than the pCN vector in a stable expression system (see Examples 5 to 7). These results suggest that the HCMV IE gene-derived transcription regulatory element induces a high level of gene expression in a transient expression system, while the human EF1α gene-derived transcription regulatory element performs better in a stable expression system.

Further, the present invention provides a chimeric expression vector having the advantages of both pCN and pEF vectors. Particularly, the chimeric expression vector pCEF of the present invention is constructed by inserting the enhancer region of HCMV IE gene into upstream of the EF1α gene promoter of pEF vector while maintaining the EF1α gene-derived transcription regulatory element comprising the promoter, the entire exon 1 sequence, the entire intron A sequence and the nucleotide sequence just before the initiation codon ATG of exon 2, which results in a high level of gene expression both in transient and stable expression systems.

It has been confirmed that the transcription efficiency of the inventive chimeric expression vector pCEF is higher than those of pEF and pCN vectors (see Example 9).

The present invention also provides a minimized eukaryotic expression vector designated pCK having a modified elementary backbone of pCN which is suitable for gene therapy using a naked DNA. Since ampicillin remaining in a DNA solution may cause an allergic reaction to some patients undergoing gene therapy, the β-lactamase gene giving ampicillin resistance is replaced with the gene giving kanamycin resistance. Furthermore, in order to minimize the vector size, all nucleotide sequences unnecessary for the vector to function as a gene delivery vehicle are removed to obtain vector pCK. A relatively high copy number of pCK can be maintained in *E. coli*. It has been confirmed that the pCK vector shows improved expression efficiency and safety (see Example 12 and 14).

Furthermore, the present invention provides a eukaryotic expression vector having a useful foreign gene introduced at the multi-cloning site. In order to examine the possibilities of using the inventive eukaryotic expression vectors as a gene delivery vehicle for gene therapy, pCN-VEGF, pEF-VEGF, pCEF-VEGF and pCK-VEGF are constructed by inserting VEGF (vascular endothelial growth factor) gene into pCN, pEF, pCEF and pCK vectors, respectively, and their expression levels of VEGF protein are measured by ELISA. The results show that these vectors produce high levels of VEGF protein both in vivo and in vitro expression systems. Accordingly, the inventive eukaryotic expression vectors can be used as a gene delivery vehicle for gene therapy.

The present invention also provides transformed microorganisms which may be obtained e.g., by transforming such *E. coli* strains as *E. coli* BL21(DE3) (Novagen, USA), *E. coli* XL-1 blue (Novagen, USA) or *E. coli* Top10 (Invitrogen, USA) with said eukaryotic expression vectors. Examples of the present invention provide such transformed microorganisms: *E. coli* Top10-pCN/VEGF, *E. coli* Top10-pEF, *E. coli* Top10-pCK, *E. coli* Top10-pCK/VEGF165 and *E. coli* Top10-pCEF. *E. coli* Top10-pCK/VEGF165 and *E. coli* Top10-pCEF have been deposited in Korean Culture Center of Microorganisms (KCCM) (Address; Yurim Bldg., 361-221, Hongje 1-dong, Seodaemun-gu, Seoul 120-091, Republic of Korea) on Dec. 27, 1999 under accession numbers KCCM-10179 and KCCM-10180, respectively; and *E. coli* Top10-pCK, *E. coli* Top10-pEF and *E. coli* Top10-pCN/VEGF, in KCCM on Mar. 31, 2003 under accession numbers KCCM-10476, KCCM-10477 and KCCM-10478, respectively, in accordance with the terms of the Budapest Treaty on the International Recognition of the Deposit of Microorganism for the Purpose of Patent Procedure.

As described above, the eukaryotic expression vectors, e.g. pCN, pEF, pCEF and pCK of the present invention can drive a high level of gene expression, and therefore, they can be effectively used as a gene delivery vehicle for gene therapy using a naked DNA in vivo for continuous expression of a foreign gene. Specifically, the use of backbone plasmid pCK having improved safety and productivity is suitable for gene therapy using a naked DNA.

Therefore, the inventive composition comprising the eukaryotic expression vector having a therapeutic gene introduced in its multi-cloning site may be used as a gene therapy agent for preventing and treating various hereditary diseases.

The composition for gene therapy of the present invention may further comprise pharmaceutically acceptable carriers. Any of the conventional procedures in the pharmaceutical field may be used to prepare oral formulations such as tablets, capsules, pills, granules, suspensions and solutions; rejection formulations such as solutions, suspensions, or dried powders that may be mixed with distilled water before injection; locally-applicable formulations such as ointments, creams and lotions; and other formulations.

Carriers generally used in the pharmaceutical field may be employed in the composition of the present invention. For example, orally-administered formulations may include binders, emulsifiers, disintegrating agents, excipients, solubilizing agents, dispersing agents, stabilizing agents, suspending agents, coloring agents or spicery. Injection formulations may comprise preservatives, unagonizing agents, solubilizing agents or stabilizing agents. Preparation for local administration may contain bases, excipients, lubricants or preservatives. Any of the suitable formulations known in the art (Remington's Pharmaceutical Science [the new edition], Mack Publishing Company, Eaton Pa.) may be used in the present invention.

The inventive composition can be clinically administered as various oral and parenteral formulations. A suitable formulation may be prepared using such excipients as additives, enhancers, binders, wetting agents, disintegrating agents and surfactants, or diluents. Solid formulations for oral administration include pills, tablets, dusting powder, granules and capsules. Those solid formulations may be prepared by mixing one or more excipients, e.g. starch, calcium carbonate, sucrose, lactose and gelatin with dibenzylbuthyllacton lignan derivatives. Also, lubricants such as magnesium stearate and talc may be included in the present formulation. Liquid formulations for oral administration include suspension, solution, emulsion and syrup. Those formulations may contain wetting agents, sweeteners, aromatics and preservatives, in addition to general simple diluents such as water and liquid paraffin. Formulations for parenteral administration include sterilized aqueous solution, suspension, emulsion, freeze-dried alternative treatment and suppositories. Water-insoluble excipients and suspending agents comprise vegetable fats such as propylene glycol, polyethylene glycol and olive oil, and injectable esters such as ethyl oleate. Witepsol®, Macrogol®, Tween® 61, cacao fats, laurin fats and glycerogelatins may be used as bases of suppositories.

The inventive composition may be administered orally or via parenteral routes such as intravenous, intramuscular, subcutaneous, intrabdominal, sternal and arterial injection or infusion, or topically through rectal, intranasal, inhalational or intraocular administration.

The typical daily dose of the active ingredient may range from 0.001 to 5 mg/kg body weight, preferably from 0.01 to 0.5 mg/kg body weight and can be administrated in a single dose or in divided dose. However, it should be understood that the amount of the effective ingredient actually administrated ought to be determined in light of various relevant factors including the conditions to be treated, the chosen route of administration, the age, sex and body weight of the individual patient, and the severity of the patient's symptom. Therefore, the above dose should not be construed as a construed as a limitation to the scope of the invention in any way.

The following examples are intended to further illustrate the present invention without limiting its scope.

EXAMPLES

Example 1

Construction of pCN

To construct a eukaryotic expression vector comprising a transcription regulatory element derived from the HCMV IE gene, a DNA fragment containing the full-length of the promoter/enhancer region (hereinafter, referred to as "$P_{CMV}$") and the nucleotide sequence upstream of the translation initiation codon of the HCMV IE gene was cloned by PCR. Vector pEQ276 (Biegalke et al., *Virology* 183:381-385, 1995) containing the nucleotide sequence region from the promoter to the exon 5 of the HCMV IE gene was used as a template and two synthetic oligonucleotides having the nucleotide sequences of SEQ ID NOs: 1 and 2 were used as a primer pair for PCR.

The amplified 1.6 kb DNA fragment has the nucleotide sequence of SEQ ID NO: 3 which comprises the promoter/enhancer, the entire exon 1, the entire intron A and the 5'-UTR of exon 2 of the HCMV IE gene. The nucleotide sequence from 1 to 599 corresponded to the $P_{CMV}$; the nucleotide sequence from 600 to 720, to the entire exon 1 sequence; the nucleotide sequence from 721 to 1547, to the entire intron A sequence; and the nucleotide sequence from 1548 to 1564, to the entire 5'-UTR of exon 2 of the HCMV IE gene. The PCR product was cloned into vector pZero-Blunt (Invitrogen) to obtain vector pZero-CMV. Then, the MluI-HindIII fragment containing the $P_{CMV}$ of vector pCDNA3.1 (Invitrogen) was replaced with the MluI-HindIII fragment of the resulting vector to obtain a vector which was designated pCN (see FIG. 1). Therefore, the elementary backbone of pCN is identical to that of pCDNA3.1 comprising a multi-cloning site, a BGH (bovine growth hormone) poly A signal (hereinafter, referred to as "pA"), an SV40 promoter (hereinafter, referred to as "$P_{SV40}$"), a neomycin resistance gene (hereinafter, referred to as "NEO") and a ColE1 origin of replication as well as the $P_{CMV}$. However, there was a difference between pCN and pCDNA3.1 in that the pCN vector has the promoter/enhancer, the entire exon 1 sequence, the entire intron A sequence and the entire 5'-UTR of exon 2 of the HCMV IE gene as a transcription regulatory element upstream of the multi-cloning site. Therefore, the foreign gene inserted into the multi-cloning site of pCN may be expressed from a spliced messenger RNA.

Example 2

Construction of pEF

To construct a eukaryotic expression vector comprising a transcription regulatory element derived from human EF1α gene, a DNA fragment containing the full-length of the promoter/enhancer region (hereinafter, referred to as "$P_{EF}$") and the nucleotide sequence upstream of the translation initiation codon of the human EF1α gene was cloned by PCR. Human genomic DNA was used as a template and two synthetic oligonucleotides having the nucleotide sequences of SEQ ID NOs: 4 and 5 were used as a primer pair for PCR.

The amplified 1.2 kb DNA fragment has the nucleotide sequence of SEQ ID NO: 6 which comprises the promoter/enhancer, the entire exon 1 sequence, the entire intron A sequence and the entire 5'-UTR of exon 2 of the human EF1α gene. The nucleotide sequence from 1 to 137 corresponded to the $P_{EF}$; the nucleotide sequence from 138 to 158, to the entire exon 1 sequence, the nucleotide sequence from 159 to 1104, to the entire intron A sequence; and the nucleotide sequence from 1105 to 1136, to the entire 5'-UTR of exon 2 of human EF1α gene. The PCR product was cloned into vector pZeroBlunt to obtain vector pZero-EF1α. Then, the MluI-NheI fragment prepared from vector pCDNA3.1 (Invitrogen) was replaced with the MluI-NheI fragment of the resulting vector to obtain a vector which was designated pEF (see FIG. 2). Since the elementary backbone of pEF is identical to that of pCDNA3.1, the pEF vector comprises a multi-cloning site, a BGH pA, a $P_{SV40}$, a NEO gene and a ColE1 origin of replication. However, the pCN vector further comprises the promoter/enhancer, the entire exon 1 sequence, the entire intron A sequence and the entire 5'-UTR of exon 2 of the human EF1α gene as a transcription regulatory element upstream of the multi-cloning site, so that a foreign gene inserted into the multi-cloning site of pEF may be expressed from a spliced messenger RNA.

*E. coli* Top10-pEF transformed by pEF vector has been deposited in Korean Culture Center of Microorganisms (KCCM) (Address; Yurim Bldg., 361-221, Hongje 1-dong, Seodaemun-gu, Seoul 120-091, Republic of Korea) on Mar. 31, 2003 under accession numbers KCCM-10477.

Example 3

Construction of pCEF

To construct a eukaryotic expression vector inducing a high level of gene expression both in transient and stable expression systems, the present inventors constructed a chimeric expression vector taking advantages of the two vectors, pCN and pEF.

The chimeric expression vector was constructed by inserting the enhancer region of HCMV IE gene into the upstream region of pEF. First, the unnecessary sequence region (from +57 to +409) of the 900 bp-long intron of pEF was removed by an internal deletion using SacII to obtain vector pEFs. The enhancer sequence of HCMV IE gene was amplified by PCR using the pCN vector as a template and two synthetic oligonucleotides having the nucleotide sequences of SEQ ID NOs: 7 and 8, as a primer pair. The PCR product was cloned into vector pCR2.1 (Invitrogen) to obtain vector pCR2.1-CMVE. Then, the BglII-SnaBI fragment containing the enhancer region of HCMV IE gene was excised from the resulting vector, and inserted into the upstream region of pEFs pre-digested with BglII-NruI to obtain a chimeric expression vector which was designated pCEF (see FIG. 3).

As a result, the chimeric expression vector pCEF comprises the HCMV IE gene-derived enhancer as well as the human EF1α gene derived promoter and the nucleotide sequence upstream of the translation initiation codon as a transcription regulatory element.

*E. coli* Top10-pCEF transformed by pCEF vector has been deposited in Korean Culture Center of Microorganisms (KCCM) (Address; Yurim Bldg., 361-221, Hongje 1-dong, Seodaemun-gu, Seoul 120-091, Republic of Korea) on Dec. 27, 1999 under accession numbers KCCM-10180.

Example 4

Effect of the Nucleotide Sequence Upstream of the Translation Initiation Codon of the HCMV IE Gene on the Gene Expression Level To examine the effect of the nucleotide sequence upstream of the translation initiation codon of the HCMV IE gene on the gene expression level, the gene expression level of pCN was compared with those of pCDNA3.1 (Invitrogen) and pCIneo (Promega). Vector pCDNA3.1 contains the promoter region of HCMV IE gene, whereas vector pCIneo contains a heterologous synthetic intron. The BamHI fragment containing a CAT reporter gene prepared from vector pCII-CAT (Korean Patent Publication No: 2000-6334) was inserted into the BamHI site of pCDNA3.1, pCIneo and pCN to obtain pCDNA3.1-CAT, pCIneo-CAT and pCN-CAT, respectively (see FIG. 4).

293T cells (DuBridge et al., *Mol. Cell Biol.* 7:379-387, 1987) were transfected with the resulting vectors pCN-CAT, pCDNA3.1-CAT and pCIneo-CAT, respectively. After 2 days transfection, the whole protein was extracted from each transfected cell and subjected to standard CAT assay as previously described (Byun et al., *Gene Therapy* 3:780-788, 1996).

TABLE 1

| Vector | CAT activity |
|---|---|
| PCDNA3.1-CAT | 0.6 (+/− 0.1) |
| pCIneo-CAT | 0.7 (+/− 0.2) |
| pCN-CAT | 37.9 (+/− 2.0) |

As shown in Table 1, the CAT activity of pCN-CAT containing the nucleotide sequence upstream of the translation initiation codon of the HCMV IE gene was 60-fold higher than those of control vectors, pCDNA3.1-CAT and pCIneo-CAT. This result suggests that the nucleotide sequence upstream of the translation initiation codon of the HCMV IE gene is responsible for the increase in the expression level of the inserted foreign gene.

Example 5

Comparison of the Gene Expression Levels of pCN, pEF and pCEF in a Transient Expression System The BamHI fragment containing a CAT reporter gene prepared from vector pCII-CAT was inserted into the BamHI site of pEF and pCEF to obtain pEF-CAT and pCEF-CAT, respectively (see FIG. 5).

293T cells were transfected with pCN-CAT, pEF-CAT and pCEF-CAT, respectively. After 2 days, the CAT activity of each reansfected cell was measured by standard CAT assay to compare the gene expression level. Using pEF as a standard, the relative gene expression levels of pCN and pCEF were calculated.

TABLE 2

| Vector | CAT activity |
|---|---|
| pCN-CAT | 7.0 +/− 2.0 |
| pEF-CAT | 1.0 |
| pCEF-CAT | 12 +/− 1.5 |

As shown in Table 2, the HCMV IE gene promoter induced a higher level of gene expression than the human EF1α gene promoter in a transient expression system where the gene expression is derived from an episomal plasmid not but from a chromosome (see FIG. 6).

Further, the CAT activity of chimeric expression vector was higher than those of pEF-CAT and pCN-CAT, respectively.

Example 6

Time-dependent Changes in the Gene Expression Level in a Stable Expression System To examine how long and how much the eukaryotic expression vectors of the present invention could express CAT gene in a stable expression system, stably transfected cell lines were generated as follows:

HeLa cells were transfected with pCN-CAT and pEF-CAT, respectively, and the transfectd cell lines were selected by using G418. The whole protein was extracted from the selected G418 resistant cells and subjected to standard CAT assay to measure the CAT activity of each cell line.

As shown in FIG. 7, the CAT activity of HeLa cells transfected with pEF-CAT was similar to that of HeLa cells transfected with pCN-CAT in a stable expression system. This result suggests that once it is integrated into the chromosome, the activity of the HCMV IE gene promoter decreases, while the activity of the human EF1α gene promoter is remains unchanged.

To confirm the above result, the CAT activities of cell lines stably transfected with pCN-CAT and pEF-CAT, respectively, were measured for 6 weeks. At the beginning, the HCMV IE gene promoter had a 3-fold higher CAT activity than the EF1α gene promoter (see FIG. 8). However, after 2 weeks, the EF1α gene promoter showed a higher CAT activity than the HCMV IE gene promoter. These results suggest that the gene expression level induced by the HCMV IE gene promoter decreases as the HCMV IE gene promoter is integrated into the chromosome.

Example 7

Comparison of the Gene Expression Levels of Subclones Transfected with pCN or pEF The activity of a cell population represents the mean value of its heterologous members. However, if it is to be used for an industrial purpose, each subclone must be characterized. Thus, a ring cloning method (Byun et al., *Gene Therapy* 3:780-788, 1996) was performed to isolate 25 subclones from the cells transfected with pCN-CAT, as well as 13 subclones from the cells transfected with pEF-CAT.

CAT activity measurements showed that 3 out of 25 subclones having the HCMV IE gene promoter showed a significantly enhanced level of CAT activity, while the rest did not express the CAT reporter gene. This result represents that most clones derived from the stably transfected cells having the HCMV IE gene promoter are inactive. In contrast, 7 out of 13 subclones having the EF1α gene promoter showed a significantly enhanced level of CAT activity (see FIG. 9). These results suggest that the promoter derived from a cellular gene such as the human EF1α gene can induce more efficient expression of a foreign gene than the promoter derived from a viral gene such as the HCMV IE gene.

Example 8

Construction of pCN-VEGF, pEF-VEGF and pCEF-VEGF

To examine the viability of using pCN, pEF and pCEF as a gene delivery vehicle for gene therapy, VEGF gene was inserted into pCN, pEF and pCEF to obtain pCN-VEGF, pEF-VEGF and pCEF-VEGF, respectively, and the VEGF expression level of each vector was measured.

cDNA encoding human VEGF121 gene was cloned by RT-PCR (reverse transcription-PCR) using a total RNA prepared from a human placenta and two synthetic oligonucleotides having the nucleotide sequences of SEQ ID NOs: 9 (sense primer) and 10 (antisense primer) as a primer pair.

The RT-PCR product was cloned into vector pCR2.1 (Invitrogen) to obtain vector pCR2.1-VEGF. The EcoRI fragment containing the VEGF gene ontained from the resulting vector was inserted into the EcoRI site of pCN, pEF and pCEF to obtain pCN-VEGF, pEF-VEGF and pCEF-VEGF, respectively (see FIG. 10).

*E. coli* Top10-pCN/VEGF transformed by the pCN-VEGF vector has been deposited in Korean Culture Center of Microorganisms (KCCM) (Address; Yurim Bldg., 361-221, Hongje 1-dong, Seodaemun-gu, Seoul 120-091, Republic of Korea) on Mar. 31, 2003 under accession numbers KCCM-10478.

Example 9

Comparison of the VEGF Expression Levels of pCN, pEF and pCEF

1) Expression Level of VEGF in Vivo

To examine the expression level of VEGF in vivo, 100 μg of the pCN-VEGF vector was injected into the anterior tibialis of 2-week old Balb/C mice. Specifically, the vector DNA was purified using an Endotoxin-free column (Quiagen, Inc.), dissolved in a PBS solution to a concentration of 2 mg/ml, and injected using an insulin injector. Two days later, the whole protein was extracted from the injected mouse muscle and subjected to ELISA (R&D systems) to measure the VEGF expression level.

As shown in FIG. 11, the VEGF expression level of pCN in the injected mouse muscle was significantly higher than that of the control.

2) Comparison of the VEGF Expression Levels of pCDNA3.1-VEGF, pCN-VEGF, pEF-VEGF and pCEF-VEGF in vivo To compare the VEGF expression levels of pCDNA3.1-VEGF, pCN-VEGF, pEF-VEGF and pCEF-VEGF in vivo, 100 μg of each vector DNA was injected into the anterior tibialis of 4-week old Balb/C mice according to the method described in (1) of Example 9. Two days later, the whole protein was extracted from the injected mouse muscle and subjected to ELISA (R&D systems) to measure the VEGF expression level.

The result showed that the VEGF expression level of pCEF was 9-fold and 3-fold higher than those of pEF and pCN, respectively (see FIG. 12).

Example 10

Construction of pCK and pCK-VEGF

In order to improve the function of pCN vector as a gene delivery vehicle for gene therapy using a naked DNA, the elementary backbone of pCN was modified as follows:

Since ampicillin left in a final DNA solution might cause an allergic reaction to some patients undergoing gene therapy, the β-lactamase gene conferring ampicillin resistance to pCN was replaced with a kanamycin resistant gene. Furthermore, all nucleotide sequences unnecessary for the vector to function as a gene delivery vehicle were removed in order to minimize the vector size, which allowed the existence of a relatively high copy number of the vector in E. coli.

The nucleotide sequences comprising the HCMV IE gene promoter, the nucleotide sequence upstream of the translation initiation codon of HCMV IE gene and a BGH pA of pCN was amplified by PCR using two synthetic oligonucleotides having the nucleotide sequences of SEQ ID NOs: 11 and 12 as a primer pair. The amplified DNA fragment was cloned into vector pCR2.1 (Invitrogen) to obtain vector pCR2.1CMVpA. The resulting vector was then treated with MluI and SalI to purify the PCR product. Then, the fragment containing the kanamycin resistance gene and ColE1 origin of replication was isolated from vector pZero2.1 (Invitrogen) by digesting with ApoI and AflIII, and ligated with the MluI/SalI fragment obtained from vector pCR2.1CMVpA, to construct a vector which was designated pCK (see FIG. 13).

E. coli Top10-pCK transformed by the pCK vector has been deposited in Korean Culture Center of Microorganisms (KCCM) (Address; Yurim Bldg., 361-221, Hongje 1-dong, Seodaemun-gu, Seoul 120-091, Republic of Korea) on Dec. 27, 1999 under accession numbers KCCM-10179.

cDNA encoding the human VEGF165 gene was cloned by RT-PCR using a total RNA prepared from human vascular smooth muscle cells as a template and two synthetic oligonucleotides having the nucleotide sequences of SEQ ID NOs: 13 and 14 as a primer pair. The amplified cDNA was cloned into vector pCR2.1 (Invitrogen) to obtain vector pCR2.1-VEGF165, and its nucleotide sequence was determined by a sequencing analysis.

The HindIII/XbaI fragment containing the VEGF165 gene obtained from the resulting vector was inserted into the HindIII/XbaI site of pCK to obtain a vector which was designated pCK-VEGF165 (see FIG. 14).

E. coli Top10-pCK/VEGF165 transformed by the pCK-VEGF165 vector was deposited in Korean Culture Center of Microorganisms (KCCM) (Address; Yurim Bldg., 361-221, Hongje 1-dong, Seodaemun-gu, Seoul 120-091, Republic of Korea) on Dec. 27, 1999 under accession number KCCM-10179.

Example 11

Construction of pCP and pCP-VEGF

A control vector pCP, whose elementary backbone is identical to that of pCK except for lacking the untranslated leader sequence of the major HCMV IE region, was constructed. The pCK vector was digested with NdeI and HindIII to remove the part of HCMV IE gene promoter, the exon 1, the intron A and the part of exon 2, and the NdeI/HindIII fragment containing the part of HCMV IE promoter obtained from vector pCDNA3.1 was inserted into the NdeI/HindIII site of pCK, to obtain vector pCP (see FIG. 15).

And then, the HindIII/XbaI fragment containing the VEGF gene obtained from the pCK-VEGF165 vector was inserted into the HindIII/XbaI site of pCP to obtain vector pCP-VEGF 165 (see FIG. 16).

On the other hand, the HidIII/XbaI fragment containing the CAT reporter gene obtained from the pCN-CAT vector was inserted into the HindIII/XbaI sites of pCK and pCP vector, to obtain pCK-CAT and pCP-CAT, respectively (see FIGS. 17 and 18).

Example 12

Comparison of the Gene Expression Levels of pCK and pCP

1) CAT expression levels of pCP and pCK in vitro

C2C12 cells (ATCC CRL-1772) were transfected with pCK-CAT and pCP-CAT, respectively, and the CAT expression level of each transfected cell was measured after 2 days. The CAT activity of pCK was found to be 30-fold higher than that of pCP (see FIG. 19).

2) VEGF Expressioon Levels of pCP and pCK in Vitro

C2C 12 cells (ATCC CRL-1772) were transfected with pCK-VEGF 165 and pCP-VEGF165, respectively, and the VEGF expression level of each transfected cell was measured after 2 days. The VEGF expression level of pCK was found to be 30-fold higher than that of pCP (see FIG. 20).

3) CAT Expressioon Levels of pCP and pCK in Vivo

100 μg doses of pCK-CAT and pCP-CAT were injected into the anterior tibialis of 2-4-week old Balb/C mice, respectively. Specifically, each vector DNA was purified using an Endotoxin-free column (Quiagen, Inc.), dissolved in a PBS solution in a concentration of 2 mg/ml, and injected using an insulin injector. Two days later, the whole protein was extracted from the injected mouse muscle and subjected to ELISA (R&D systems: n=40) to measure the CAT expression level.

As shown in FIG. 21, the CAT expression level of pCK was 30-fold higher than that of pCP.

4) VEGF Expressioon Levels of pCP and pCK in Vivo

100 μg doses of pCK-VEGF165 and pCP-VEGF165 were injected into the anterior tibialis of 2-4-week old Balb/C male mice, respectively. Specifically, each vector DNA was purified using an Endotoxin-free column (Quiagen, Inc.), dissolved in a PBS solution in a concentration of 1 mg/ml, and injected using an insulin injector. The whole protein was extracted from the injected mouse muscle and subjected to ELISA (R&D systems: n=41) to measure the VEGF expression level.

The pCK vector was found to induce a higher level of VEGF expression than the pCP vector in vivo, which suggests that the former is a more effective gene delivery vehicle for gene therapy (see FIG. 22).

Example 13

Construction of pCP2 and pCP2-VEGF

Another control vector pCP2, whose elementary backbone is identical to that of pCK except for lacking 9 bp of the untranslated leader sequence of the exon 2 of the major HCMV IE region, was constructed. The DNA fragment containing the nucleotide sequence from 1 to 1555 of SEQ ID NO: 3 was cloned by PCR. Vector pCK was used as a template and two synthetic oligonucleotides having the nucleotide sequences of SEQ ID NOs: 1 and 15 were used as a primer pair for PCR.

The PCR product was cloned into vector pZeroBlunt (Invitrogen) to obtain vector pZero-CMV2. Then the pCK vector was digested with NdeI and HindIII to remove the part of HCMV IE gene promoter, the exon 1, the intron A and the part of exon 2, and the NdeI/HindIII fragment containing the nucleotide sequence from 1 to 1555 of SEQ ID NO: 3 obtained from pZero-CMV2 was inserted into the NdeI/HindIII site of pCK, to obtain vector pCP2.

And then, the HindIII/XbaI fragment containing the VEGF gene obtained from the pCK-VEGF165 vector was inserted into the HindIII/XbaI site of pCP2 to obtain vector pCP2-VEGF.

On the other hand, the HidIII/XbaI fragment containing the CAT reporter gene obtained from vector pCN-CAT was inserted into the HindIII/XbaI site of pCP2 vector, to obtain pCP2-CAT.

Example 14

Comparison of the Gene Expression Levels of pCK and pCP2

1) CAT Expressioon Levels of pCK and pCP2 in Vitro

C2C12 cells (ATCC CRL-1772) were transfected with pCK-CAT and pCP2-CAT, respectively, and the CAT expression level of each transfected cell was measured after 2 days.

TABLE 3

| Vector | Relative CAT activity |
|---|---|
| pCK-CAT | 2.1 +/− 0.5 |
| pCP2-CAT | 1.0 |

As shown in table 3, the CAT activity of pCK was found to be 2-fold higher than that of pCP2.

2) VEGF Expressioon Levels of pCK and pCP2 in Vitro

C2C12 cells (ATCC CRL-1772) were transfected with pCK-VEGF165 and pCP2-VEGF165, respectively, and the VEGF expression level of each transfected cell was measured after 2 days.

TABLE 4

| Vector | Relative VEGF level |
|---|---|
| pCK-VEGF165 | 2.3 +/− 0.7 |
| pCP2-VEGF165 | 1.0 |

As shown in table 4, the VEGF expression level of pCK was found to be 2-fold higher than that of pCP2.

3) CAT Expressioon Levels of pCK and pCP2 in Vivo

100 μg of pCK-CAT and pCP2-CAT were injected into the anterior tibialis of 2-4-week old Balb/C mice, respectively. Specifically, each vector DNA was purified using an Endotoxin-free column (Quiagen, Inc.), dissolved in a PBS solution in a concentration of 2 mg/ml, and injected using an insulin injector. Two days later, the whole protein was extracted from the injected mouse muscle and subjected to ELISA (R&D systems: n=25) to measure the CAT expression level.

TABLE 5

| Vector | Relative CAT activity |
|---|---|
| pCK-CAT | 2.2 +/− 0.7 |
| pCP2-CAT | 1.0 |

As shown in Table 5, the CAT expression level of pCK was 2-fold higher than that of pCP2.

4) VEGF Expressioon Levels of pCK and pCP2 in Vivo

100 μg of pCK-VEGF165 and pCP2-VEGF165 were injected into the anterior tibialis of 2-4-week old Balb/C male mice, respectively. Specifically, each vector DNA was purified using an Endotoxin-free column (Quiagen, Inc.), dissolved in a PBS solution in a concentration of 2 mg/ml, and injected using an insulin injector. The whole protein was extracted from the injected mouse muscle and subjected to ELISA (R&D systems: n=25) to measure the VEGF expression level.

TABLE 6

| Vector | Relative VEGF level |
|---|---|
| pCK-VEGF165 | 2.3 +/− 0.8 |
| pCP2-VEGF165 | 1.0 |

As shown in Table 6, the pCK vector was found to induce a higher level of VEGF expression than the pCP2 vector in vivo, which suggests that the former is a more effective gene delivery vehicle for gene therapy.

Example 15

Time-dependent Changes in the Gene Expression Level

1) CAT Expression Level in Vivo

In order to determine the pharmaceutical kinetics of CAT expression in vivo, 100 μg of pCK-CAT vector was injected into the anterior tibialis of 2-4-week old Balb/C male mice according to the method described in Example 12. The whole protein was extracted from the injected mouse muscle every 2 day over a period of 2 weeks and subjected to ELISA (R&D systems: n=30) to measure the CAT expression level.

The CAT expression was sustained for 2 weeks after injection (see FIG. 23).

2) VEGF Expression in Vivo

In order to determine the pharmaceutical kinetics of VEGF expression in vivo, 100 μg of pCK-VEGF165 was injected into the anterior tibialis of 2-4-week old 12 Balb/C male mice according to the method described in Example 12. The whole protein was extracted from the injected mouse muscle every 2 day over a period of 2 weeks and subjected to ELISA (R&D systems: n=30) to measure the VEGF expression level.

The VEGF expression was sustained for 2 weeks after injection (see FIG. 24).

Example 16

Dose-dependency of Gene Expression

1) Dose-dependency of the CAT Expression in Vivo

To examine the effect of vector concentration on the gene expression level, varying doses of the pCK-CAT vector ranging from 50 to 500 μg/mouse were injected to 2-4-week old Balb/C male mice according to the method described in Example 12. After 2 days, the whole protein was extracted from the injected mouse muscle and subjected to ELISA (R&D systems: n=30) to measure the CAT expression level.

The result showed that the injected amount of pCK-CAT was dependent upon the CAT expression level (see FIG. 25).

2) Dose-dependency of the VEGF Expression in Vivo

To examine the effect of vector concentration on the gene expression level, varying doses of the pCK-VEGF vector ranging from 25 to 500 μg/mouse were injected to 2-4-week old Balb/C male mice according to the method described in Example 12. After 2 days, the whole protein was extracted from the injected muscle and subjected to ELISA (R&D systems: n=8-10) to measure the VEGF expression level.

As a result, it was confirmed that the injected amount of pCK was dependent upon the VEGF expression level (see FIG. 26).

Example 17

Virus Packaging Efficiency of pCN

A gag-pol expression vector and an env expression vector having the elementary backbone of pCN were constructed in order to examine the retrovirus packaging efficiency of pCN. To distinguish the selectable marker gene from an inherent neomycin gene of retroviral vector, a puromycin resistance gene was employed for the gag-pol expression vector and a hygromycin resistance gene, for the env expression vector as the selectable marker gene.

1) Construction of Gag-pol Expression Vector

The pCPu-gag•pol vector having the puromycin gene as a eukaryotic selectable marker gene, and the enhancer/promoter and the nucleotide sequence upstream of the translation initiation codon of the HCMV IE gene as a transcription regulatory element was constructed as follows:

First, the NEO gene was deleted from vector pCI-neo (Promega) by digesting with AvrII and BamHI, and then, the EcoRI-BglII fragment containing the puromycin resistance gene obtained from the pCII-puro vector was inserted into the AvrII-BamHI site of the resulting vector to obtain vector pCI-puro. After the HCMV IE promoter was removed from the pCI-puro vector by digesting with BglII and NheI, the MulI-HindIII fragment containing the promoter and the nucleotide sequence upstream of the translation initiation codon of HCMV IE gene obtained from the pCN vector was inserted into the BglII-NheI site of the resulting vector to obtain a vector which was designated pCPu (see FIG. 27).

On the other hand, the gag-pol fragment derived from MLV (murine leukemia virus) was amplified by PCR using the conventional gag-pol expression vector, pHIT60 (Cannon et al., J. Virol. 70:8234-8240, 1996) as a template and two synthetic oligonucleotides having the nucleotide sequences of SEQ ID NOs: 16 and 17, as a primer pair. The amplified gag-pol fragment was inserted into the pCII vector (Invitrogen) to obtain vector pCII-gag/pol.

The gag-pol fragment was then purified from the pCII-gag/pol vector by digesting with NheI and NotI and was inserted into the MluI-NotI site of vector pCPu to construct a gag-pol expression vector, pCPu-gag•pol (see FIG. 28).

2) Construction of env Expression Vector

The pCH-env vector having the hygromycin resistance gene as a eukaryotic selectable marker gene, and the enhancer/promoter and the nucleotide sequence upstream of the translation initiation codon of the HCMV IE gene as a transcription regulatory element was constructed as follows:

First, the NEO gene was deleted from vector pCI-neo (Promega) by digesting with StuI and HindIII, and then, the PvuI-HindIII fragment containing the hygromycin resistance gene and MMTV (mouse mammary tumor virus) LTR (long terminal repeats) derived from the pCII-MMTVhyg vector was inserted into the StuI-HindIII site of the resulting vector to obtain vector pCI-hygro. After the HCMV IE promoter was purified from the pCI-hygro vector by digesting with BglII and NheI, the MluI-HindIII fragment containing the promoter and the nucleotide sequence upstream of the translation initiation codon of the HCMV IE gene obtained from the pCN vector was inserted into the BglII-NheI site of the resulting vector to obtain vector pCH (see FIG. 29).

On the other hand, the env fragment derived from MLV (Cannon et al., J. Virol. 70:8234-8240, 1996) was amplified by PCR using the conventional vector, pHIT456 (Cannon et al., J. Virol. 70:8234-8240, 1996) as a template and two synthetic oligonucleotides having the nucleotide sequences of SEQ ID NOs: 18 and 19 as a primer pair. The amplified env fragment was inserted into the pCII vector (Invitrogen) to obtain vector pCII-env.

The env fragment was then purified from the pCII-env vector by digesting with NheI and NotI and was inserted into the MluI-NotI site of pCH vector to construct an env expression vector, pCH-env (see FIG. 30).

3) Examination of Retrovirus Packaging Efficiency

To compare the retrovirus packaging efficiencies of pCPu-gag•pol and pCH-env vectors with that of the conventional packaging vector, 293T cells were transfected with the retrovirus vector MFG-CAT (Kim et al., J. Virol. 72:994-1004, 1998) together with pCPu-gag•pol and pCH-env, respectively, and cultured for 48 hours. Cell-free viral supernatants were obtained by filtrating the culture solutions with 0.45 μm filter.

And then, NIH3T3 cells (ATCC CRL 1658) were then transfected with each cell-free viral supernatant and cultured for 48 hours. The cytosolic protein was extracted from each transfected cell and subjected to ELISA (R&D systems) to measure the CAT activity.

TABLE 7

| Packaging vector | CAT activity |
|---|---|
| pHIT456, pHIT60 | 50 +/− 10 |
| pCPu-gag · pol, pCH-env | 60 +/− 10 |

As shown in Table 7, the retrovirus packaging efficiencies of pCPu-gag•pol and pCH-env are higher by about 20% than those of the conventional vectors, pHIT456 and pHIT60.

Example 18

Acute Toxicity Test by Parenteral Administration

Acute toxicity tests were performed using 5 groups (5 mice/group) of 4-week old Balb/C SPF mice, and each group of mice were injected with varying doses of pCK-VEGF165 which increased by 0.5 mg/kg upto a maximum doses of 50 mg/kg. The vector DNA was dissolved in isotonic water, and 200 μl of the solution was injected into the anterior tibialis of each mouse.

4-week old SD SPF rats were also divided by 5 groups (5 rats/group), and each group of rats were injected with varying doses of pCK-VEGF165 which increased by 0.5 mg/kg upto a maximum doses of 200 mg/kg. The vector DNA was dissolved in isotonic water, and 500 μl of the solution was injected into the anterior tibialis of each rat.

An equal amount of PBS was administrated to a control group. After a week administration, death, clinical diagnosis and change of weight of the animals are observed. Then, the animals were autopsied to observe the possible disorders of internal organs.

In every animal tested, no disorder induced by administering the VEGF expression vector was found. Consequently, the minimal lethal dose of pCK-VEGF is higher than 50 mg/kg for mouse and higher than 200 mg/kg for rat.

Example 19

Gene Therapy Employing pCK-VEGF165 in a Rabbit Ischemic Hind Limb Model

In order to examine whether pCK vector is effective in the treatment of ischemic hind limb disease, gene therapy was carried out on a rabbit ischemic hind limb model as follows.

A rabbit ischemic hind limb model, which is a standard animal model for the ischemic limb disease, was prepared by the method described by Takeshita et al. (*Journal of Clinical Investigation* 93:662, 1994). At the day before operation (Day 0), each of 45 white rabbits from New Zealand (male, from 3.8 to 4.2 kg) was intramuscularly injected with 5 mg/kg of xylazine and, then, anesthetized by an intramuscular injection of 50 mg/kg of ketamine. Subsequently, the left femoral region of the rabbit was incised and all branches of the femoral artery were separated and tied. The region from the proximal part to the branching point of the saphenous and popliteal arteries was incised to prepare the model. After the operation, 15 mg/kg/day of cefazolin was injected intramuscularly for 5 days and 0.3 mg/day of morphin, for 10 days. 10 days after the operation (Day 10), angiography was carried out for the left hind limb where the ischemia was induced, and the degree of arteriogenesis was recorded as a basal level. The rabbits were randomly divided into three groups and injected at four sites in the femoral muscle with 500 μg of plasmid pCK-VEGF165 (Experimental group), 500 μg of plasmid pCP-VEGF165 (Control group), or 500 μg of plasmid pCK, respectively. 40 days after the operation (Day 40), angiography was carried out again for the left hind limb and the degree of arteriogenesis at the arteriole level was determined and compared to that of Day 10.

TABLE 8

| Vector | Relative number of angiographical vessels |
| --- | --- |
| pCK | 1.0 |
| pCK-VEGF165 | 2.8 +/− 0.5 |
| pCP-VEGF165 | 1.1 +/− 0.3 |

As can be seen from the result in table. 8, the number of angiographical vessels was significantly increased in the experimental group administered with pCK-VEGF165 as compared with the pCP-VEGF165 or pCK administered control group. This result demonstrates that pCK vector can be effectively used in the gene therapy of an ischemic disease.

---

What is claimed is:

1. A transcription regulatory element operably linked to a heterologous coding sequence, the transcription regulatory element consisting of the nucleotide sequence of SEQ ID NO: 3.

2. A eukaryotic expression vector comprising the transcription regulatory element of claim 1.

3. The vector of claim 2, further comprising a ColE1 origin of replication in operable association with said transcription regulatory element.

4. The vector of claim 3, further comprising a poly A signal in operable association with said transcription regulatory element.

5. The vector of claim 2, further comprising a selectable marker gene in operable association with said transcription regulatory element.

6. The vector of claim 2, further comprising a multi-cloning site in operable association with said transcription regulatory element.

7. The vector of claim 6, wherein said transcription regulatory element is located upstream of said multi-cloning site.

8. The vector of claim 7, further comprising a ColE1 origin of replication in operable association with said transcription regulatory element.

9. The vector of claim 8, further comprising a poly A signal in operable association with said transcription regulatory element.

10. The vector of claim 9, wherein said poly A signal is a BGH poly A signal.

11. The vector of claim 10, further comprising a selectable marker gene in operable association with said transcription regulatory element.

12. The vector of claim 11, wherein said selectable marker gene is an ampicillin resistance gene.

13. The vector of claim 2, further comprising:
a multi-cloning site;
a ColE1 origin of replication;
a polyA signal; and
a selectable marker gene;
wherein said multi-cloning site; said ColE1 origin of replication; said polyA signal; and said selectable marker gene are in operable association with said transcription regulatory element.

14. The vector of claim 13, wherein said selectable marker gene is an ampicillin resistance gene.

15. The vector of claim 13, wherein said vector is pCN.

16. The vector of claim 13, wherein said selectable marker gene is a kanamycin resistance gene.

17. The vector of claim 13, wherein said vector is pCK.

18. The vector of claim 7, further comprising a nucleotide sequence of interest within said multi-cloning site.

19. The vector of claim 18, wherein said nucleotide sequence of interest is a cDNA encoding a human VEGF.

20. The vector of claim 19, wherein said human VEGF is VEGF165.

21. The vector of claim 20, wherein said vector is pCN/VEGF or pCK/VEGF.

22. A method of delivering a polypeptide into a eukaryotic cell comprising the step of contacting said eukaryotic cell with the vector of any one of claims 18-21.

23. A method of delivering a polypeptide into a mammal comprising the step of administering to the mammal the vector of any one of claims 18-21.

24. An isolated cell transformed with the eukaryotic expression vector of any of claims 1-21, said cell being a microorganism or an animal cell.

25. The cell of claim 24, wherein the cell is selected from the group consisting of *Escherichia coli* Top 10-pCN/VEGF (KCCM-10478); *Escherichia coli* Top 10-pCK (KCCM-10476); and *Escherichia coli* Top 10-pCK/VEGF 165 (KCCM-10179).

26. A gag-pol expression vector comprising the transcription regulatory element of claim 1.

27. The gag-pol expression vector of claim 26, wherein said vector comprises a gag-pol fragment derived from an MLV.

28. The gag-pol expression vector of claim 27, wherein said vector is pCPu-gag.pol.

29. An env expression vector comprising the transcription regulatory element of claim 1.

30. The env expression vector of claim 29, wherein said vector is pCH-env.

* * * * *